United States Patent
Brenin et al.

(10) Patent No.: US 11,617,901 B2
(45) Date of Patent: Apr. 4, 2023

(54) APPLICATION OF RADIATION USING IMAGING GUIDANCE

(71) Applicant: University of Virginia Patent Foundation, Charlottesville, VA (US)

(72) Inventors: David R. Brenin, Charlottesville, VA (US); Timothy Norman Showalter, Charlottesville, VA (US); John A. Hossack, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 1007 days.

(21) Appl. No.: 16/401,944

(22) Filed: May 2, 2019

(65) Prior Publication Data

US 2019/0336792 A1 Nov. 7, 2019

Related U.S. Application Data

(60) Provisional application No. 62/665,580, filed on May 2, 2018.

(51) Int. Cl.
*A61N 5/10* (2006.01)

(52) U.S. Cl.
CPC ......... *A61N 5/1027* (2013.01); *A61N 5/1002* (2013.01); *A61N 5/1031* (2013.01); *A61N 5/1048* (2013.01)

(58) Field of Classification Search
CPC .. A61N 5/1027; A61N 5/1002; A61N 5/1031; A61N 5/1048; A61N 5/1015; A61N 5/1014; A61N 5/10; A61N 2005/1018; A61N 2005/1003; A61N 2005/1058
See application file for complete search history.

(56) References Cited

U.S. PATENT DOCUMENTS

| | | | | |
|---|---|---|---|---|
| 5,391,139 A | * | 2/1995 | Edmundson | A61N 5/103 600/7 |
| 5,707,332 A | * | 1/1998 | Weinberger | A61N 5/1002 600/3 |
| 5,810,007 A | * | 9/1998 | Holupka | A61B 8/12 600/407 |
| 6,416,492 B1 | * | 7/2002 | Nielson | A61N 5/1002 600/467 |

(Continued)

OTHER PUBLICATIONS

"Brachytherapy Market Recovery to Reach US$ 2.4 Billion", MEDraysintell, [Online]. [Accessed May 28, 2019]. Retrieved from the Internet: URL: http: web.archive.org web 20160308045436 https: www.prlog.org 12390829-brachytherapy-market-recovery-to-reach-US-2-4-billion.htmlArchived date—Mar. 8, 2016, (Nov. 4, 2014), 3 pgs.

(Continued)

*Primary Examiner* — Samuel G Gilbert
(74) *Attorney, Agent, or Firm* — Schwegman Lundberg & Woessner, P.A.

(57) ABSTRACT

Apparatus or techniques can include an applicator that can include an expandable element and an ultrasonic transducer. The applicator can be inserted into a cavity of a tissue region of a patient and images of the cavity and the applicator can be generated based on signals obtained from the ultrasonic transducer. Dosing of radiation can be determined based on the images and a dose of radiation can be delivered to the tissue region by a radiation source located in the applicator.

20 Claims, 16 Drawing Sheets

(56) References Cited

U.S. PATENT DOCUMENTS

| | | | |
|---|---|---|---|
| 6,610,013 B1 | 8/2003 | Fenster et al. | |
| 7,172,796 B2* | 2/2007 | Kinoshita | A61L 29/126 |
| | | | 428/36.1 |
| 2010/0239144 A1* | 9/2010 | Fichtinger | A61N 5/1027 |
| | | | 382/131 |
| 2018/0071549 A1* | 3/2018 | Krechting | A61B 8/4281 |

OTHER PUBLICATIONS

"Dosimetric comparison of Ir high-dose-rate brachytherapy vs. 50 kV x-rays as techniques for breast intraoperative radiation therapy: Conceptual development of image-guided intraoperative brachytherapy using a multilumenballoonapplicatorandin-roomCTimaging", Brachytherapy; 13(5):502-7 doi: 10.1016 j.brachy.2014.04.00, (2014), 6 pgs.

Pluim, Josien P.W., "Mutual-Information-Based Registration of Medical Images: A Survey", IEEE Transactions on Medical Imaging, vol. 22, No. 8, 986-1004, (Aug. 2003), 19 pgs.

Trifiletti, D.M., "Intraoperative breast radiation therapy with image guidance: Findings from CT images obtained in a prospective trial of intraoperative high-dose-rate brachytherapy with CT on rails", Brachytherapy. 14(6): p. 919-924, (2015), 6 pgs.

Yu, Yongjian, "Speckle reducing anisotropic diffusion", IEEE Transactions On Image Processing, vol. 11, No. 1; 1260-1270, (Nov. 2002), 11 pgs.

* cited by examiner

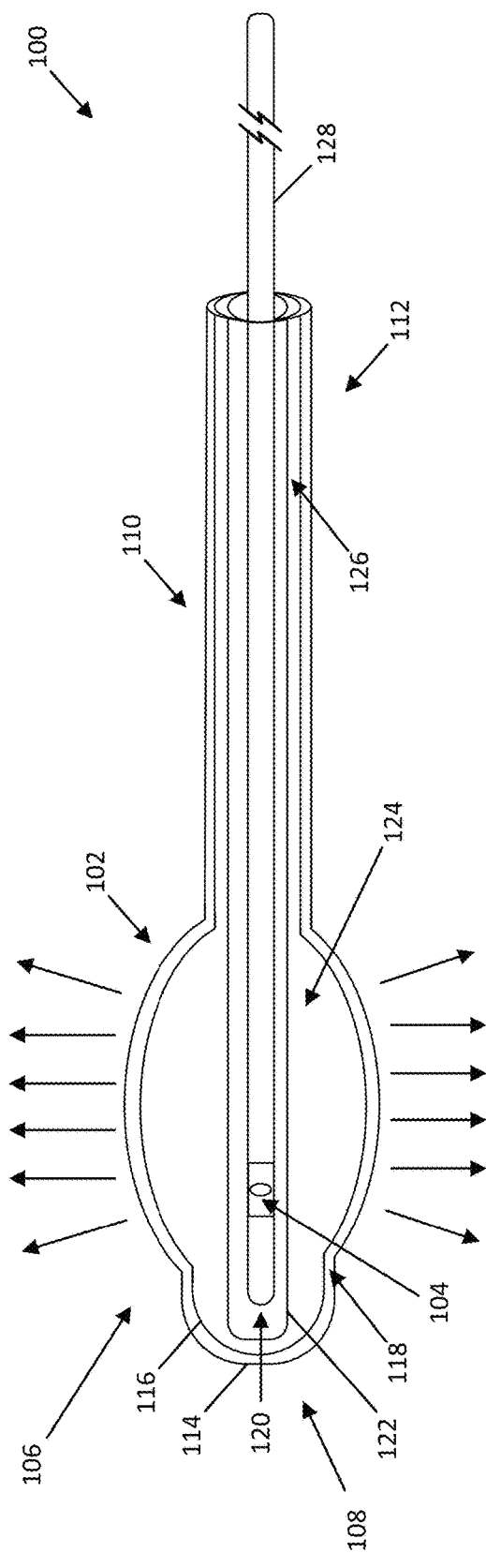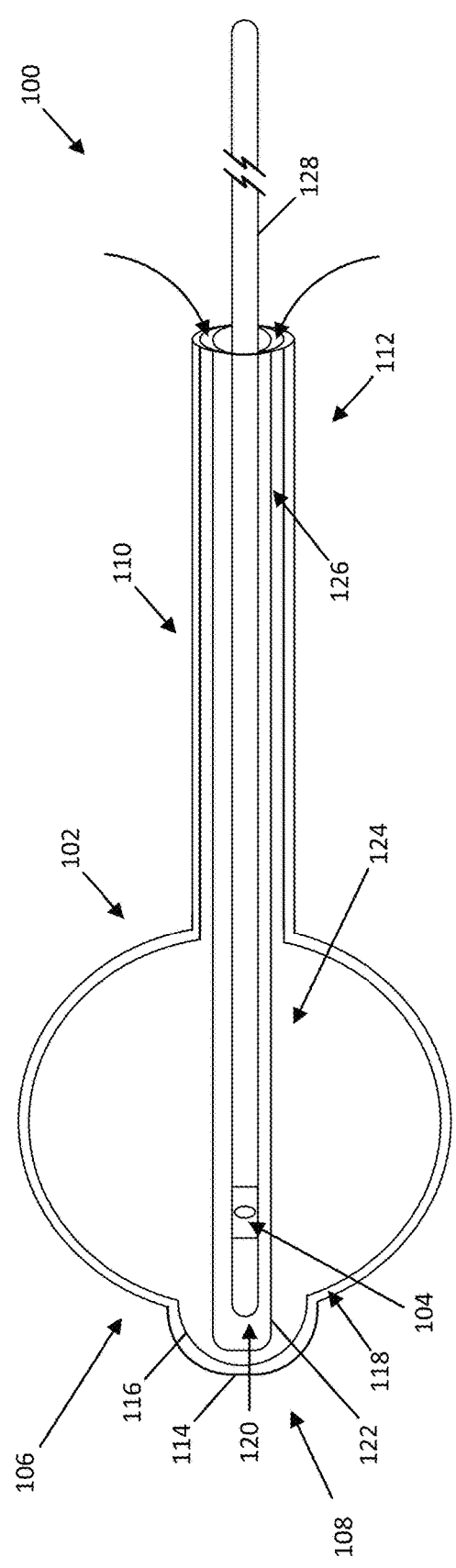

US 11,617,901 B2

APPLICATION OF RADIATION USING IMAGING GUIDANCE

CLAIM OF PRIORITY

Benefit of priority is hereby claimed to U.S. Provisional Patent Application Ser. No. 62/665,580, titled "Real-Time Ultrasound Guidance for Breast Cancer Margin Oncology Procedures," filed on May 2, 2018, which is hereby incorporated by reference herein in its entirety.

BACKGROUND

Radiation therapy can be used to treat various cancers. In some instances, radiation therapy can be a primary method of treatment for cancer, while in other situations, radiation therapy can supplement another method of treatment, such as surgical removal of a tumor or chemotherapy. External beam radiotherapy (EBRT) often follows tumor removal surgery to help prevent reoccurrence of the cancer. However, there can be delays between surgical removal of the tumor and EBRT, which can increase the likelihood of tumor cell regrowth and EBRT may take place over several weeks. Additionally, with EBRT, it can be difficult to localize the application of the radiation dose to the surgical site and minimize the damage done by the radiation treatment to tissue outside of the site where the tumor was removed.

Intraoperative radiation therapy (IORT) can be used in place of or to supplement EBRT. IORT involves the delivery of radiation to a surgical site, often using the same incision that was used to remove the tumor. In this way, the radiation treatment can be delivered to the tumor bed soon after removal of the tumor and before the surgical site is closed. Additionally, a localized dose of radiation can be delivered to the surgical site while minimizing exposure of tissue outside of the surgical site to radiation. The radiation dose can be delivered, in various instances, using a point source of x-rays, such as a spherical applicator or a cylindrical applicator. High dose rate (HDR) brachytherapy is a form of IORT that includes the delivery of relatively high doses of radiation to the tumor bed for a relatively short period of time, such as from about 20 minutes to about 45 minutes.

BRIEF DESCRIPTION OF THE DRAWINGS

FIG. 1A illustrates generally an example of at least a portion of an apparatus that includes an ultrasonic transducer and an expandable element.

FIG. 1B illustrates generally an example of at least a portion of an apparatus that includes an ultrasonic transducer and an expandable element that has been inflated.

Figure 2:
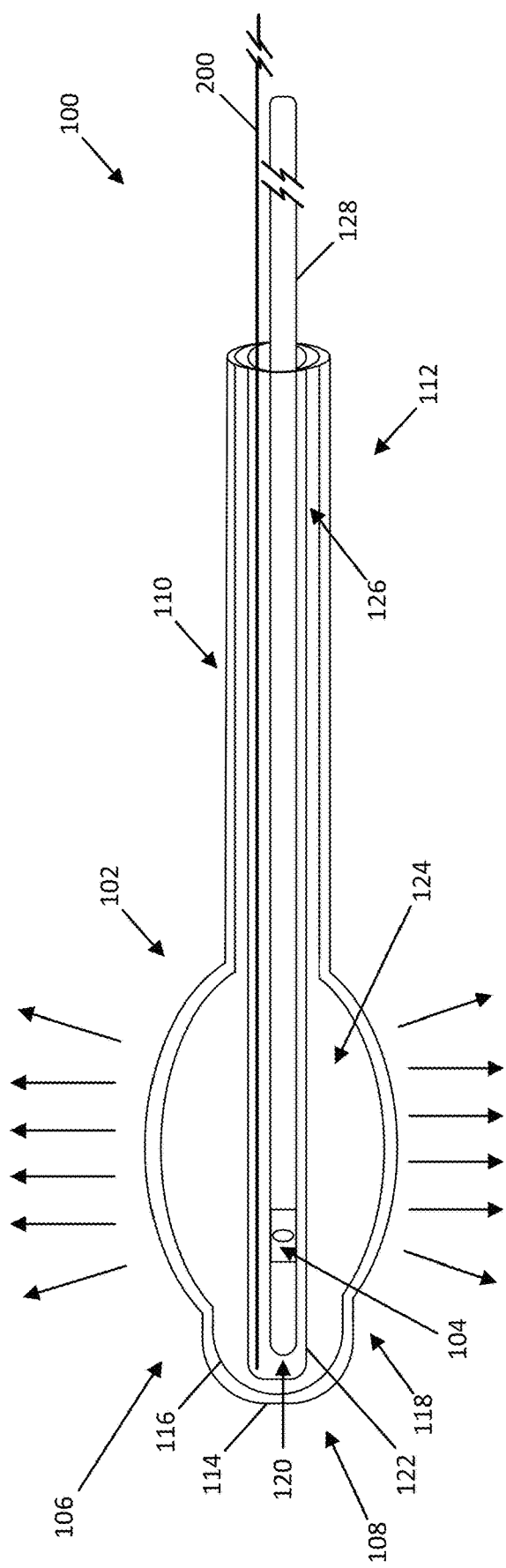
FIG. 2 illustrates generally an example of at least a portion of an apparatus that includes an ultrasonic transducer, a guide wire for a radiation source, and an expandable element.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In one approach, radiation applicators can be used to deliver a dose of radiation to a site where a tumor resides or a site where a tumor has been removed. The applicators can be placed such that the dose of radiation is delivered under the surface of the skin of a patient. However, in conventional approaches, the size of the site being treated is unknown. In particular, without information about the site in which the applicator is placed, the volume of the to which the radiation is delivered is unknown. Accordingly, the dosing of the radiation is typically a generic amount and is applied using a relatively simply delivery system with no ability to sculpt or customize the radiation dose. Thus, the dose of radiation delivered to a patient can be less than the dose needed to effectively provide treatment to the patient based on the size of the site or the dose of radiation delivered to a patient can be more than the dose needed to effectively provide treatment to the patient based on the size of the site. In situations where a dose delivered to the treatment site is too low, a reduction in the effectiveness of the treatment can occur. Additionally, in situations where a dose delivered to the treatment site is too high, unnecessary damage can occur to cells at the treatment site and to additional cells adjacent to the treatment site. The presence of air voids in the vicinity of the applicator needed to be known as this can impact the choice of dosing—or may suggest adjustment of applicator location to minimize air voids. The presence and adjacency of skin surface and rib bones are also factored into choice of radiation and dosing.

In contrast, techniques and implementations are described herein that can enable the customization of radiation doses delivered to patients and that can improve the effectiveness of radiation treatment delivered to a patient. For example, imaging devices can be used to provide representations of the sites to which radiation can be delivered. Clinicians can, based on the representations, modify a shape of an applicator and/or a shape of the site in which the applicator is placed to conform the contours of the applicator with those of the site. As a result, the configuration of the applicator can be adjusted to deliver radiation more accurately throughout the site. Additionally, the amount of radiation delivered to the site can be more accurately determined due to the ability to calculate the volume of the site based on the representations. In this way, appropriate amounts of radiation can be delivered to a treatment site in contrast to conventional techniques while minimizing the risk of exposure of cells at the site and adjacent to the site to excess radiation.

In various examples, a tumor can be removed from a patient and a cavity can be formed within the patient where the tumor was previously located. A clinician can insert an applicator into the cavity through the incision site that was used to remove the tumor. Imaging techniques can then be implemented to generate 2-dimensional (2D) or 3-dimensional (3D) representations of the cavity and the location of the applicator within the cavity. The representations can indicate features, such as air gaps within the cavity where the applicator is not present, bone, and the skin surface. The image techniques can include at least one of computed tomography (CT), ultrasound, magnetic resonance (MR), or positron emission tomography (PET). If needed, the configuration of the applicator and/or the shape of the cavity can be modified by a clinician to minimize the air gaps. Additionally, dosing calculations can be performed based on a volume indicated by the representations. For example, the applicator can be a multi-lumen applicator that includes a number of lumens that can each house a radiation source during treatment of the patient. The positioning of the radiation sources within the individual lumen and the intensity and/or time that the individual radiation sources are active can be based on at least one of volume of the cavity or shape of the cavity indicated by the representations.

In one or more approaches, the applicator can include at least one lumen that houses an ultrasonic transducer. The applicator can be placed within a cavity of a patient and the ultrasonic transducer can transmit acoustic energy and receive signals indicating scattering or reflection of the acoustic energy. The signals received in response to the transmission of the acoustic energy can be used to generate a visual representation of the cavity. In one or more examples, the applicator can also include at least one lumen that houses a guide wire for a radiation source. Thus, in various implementations, the applicator can be used as both an imaging device and a device to deliver a dose of radiation. In one example, the ultrasonic transducer and the guide wire for the radiation source can be located within a same lumen, while in additional examples, the applicator can include a central lumen that houses the ultrasonic transducer and one or more additional lumen that are separate from the central lumen that houses one or more guide wires for the radiation source.

FIG. 1A illustrates generally an example of at least a portion of an apparatus 100 that includes an expandable element 102 and an ultrasonic transducer 104. The apparatus 100 can comprise an elongate member 106 that includes the expandable element 102 at a distal end 108 of the elongate member 106 and an axial element 110 that includes a proximal end 112 of the elongate member 106. The elongate member 106 can have an outer surface 114 and an interior surface 116 that defines an outer wall region 118. The outer wall region 118 can include one or more polymeric materials. For example, the outer wall region 118 can comprise at least a silicone-containing material.

In addition, the elongate member 106 can include a lumen 120 defined by a boundary surface 122. An interior region 124 can be disposed between the boundary surface 122 and the interior surface 116. The interior region 124 can have an expandable volume. For example, the interior region 124 can be filled with a fluid such that pressure is exerted by the fluid in the interior region 124 onto the interior surface 116 causing the volume of the interior region 124 to increase, which in turn, results in the expansion of the expandable element 102. In the illustrative example of FIG. 1A, the fluid disposed within the interior region 124 has not caused expansion of the expandable element 102. The fluid can be added to the interior region 124 via a channel 126 located in the axial element 110. The fluid is, ideally, degassed by means of placing in vacuum for a period of several minutes. The fluid is typically degassed water.

In examples, both the lumen 120 and the interior region 124 can be filled with a fluid. For example, the lumen 120 and the interior region 124 can be filled with a gas. In additional examples, the lumen 120 and the interior region 124 can be filled with a liquid. The lumen 120 and the interior region 124 can be filled with a same fluid in various instances, while in other situations, the lumen 120 and the interior region 124 can be filled with a different fluid. In illustrative examples, at least one of the lumen 120 or the interior region 124 can be filled with an aqueous solution, such as water.

The apparatus 100 can also include a second elongate member 128 that includes the ultrasonic transducer 104. The second elongate member 128 can be removably disposed within the lumen 120. In examples, the second elongate member 128 can slide into and out of the lumen 120. In one or more examples, the second elongate member 128 can also include a rotating drive shaft that enables transmission of acoustic energy radially by the ultrasonic transducer 104.

The elongate member 106 and the second elongate member 128 can have a number of lengths. In examples, a length of the elongate member 106 can be different from a length of the second elongate member 128. A length of the elongate member 106 can, in one or more examples, be from about 5 cm to about 30 cm, from about 7 cm to about 25 cm, or from about 10 cm to about 20 cm. A length of the second elongate member 128, in one or more examples, can be from about 10 cm to about 200 cm, from about 25 cm to about 150 cm, or from about 50 cm to about 125 cm.

FIG. 1B illustrates generally an example of at least a portion of an apparatus 100 that includes an expandable element 102 that has been inflated and that includes an ultrasonic transducer 104. To illustrate, fluid can be introduced into the interior region 124 of the elongate member 106 via the channel 126 as shown by the arrows at the proximal end 112 of the elongate member 106. After a sufficient volume of the fluid has been added to the interior region 124, the fluid can exert pressure on the interior surface 116 and cause the expandable element 102 to inflate. In examples, introducing fluid into the interior region 124 can cause the expandable element 102 to increase in volume to at least 2 times an initial volume of the interior region 124, at least 3 times the initial volume of the interior region 124, at least 4 times the initial volume of the interior region 124, or at least 5 times the initial volume of the interior region 124. The initial volume of the interior region 124 can represent a volume of the interior region 124 in the absence of sufficient pressure exerted by fluid inside the interior region 124 on the interior surface 116 to cause the expandable element 102 to expand. The fluid can be deposited into the interior region 124, in illustrative examples, using an inflation device (not shown) coupled to the proximal end 112 of the elongate member 106. In additional implementations, the inflation device can be an extension of the elongate member 106 and be formed as part of the elongate member 106. The inflation device can be coupled to a fluid source that can be operated to inject the fluid into the interior region 124.

FIG. 2 illustrates generally an example of at least a portion of an apparatus 100 that includes an ultrasonic transducer 104, a delivery device 200 for a radiation source, such as a guide wire, and an expandable element 102. Both the radiation source delivery device 200 and the second elongate member 128 that includes the ultrasonic transducer 104 can be located within the lumen 120. The radiation source delivery device 200 can be removably disposed within the lumen 120. For example, the radiation source delivery device 200 can slide into and out of the lumen 120. In illustrative examples, the radiation source delivery device 200 can be hollow and a radiation source can be placed within the interior of the radiation source delivery device 200. In additional examples, the radiation source delivery device 200 can include material that emits radiation to treat biological conditions, such as cancer. In one or more examples, the radiation source delivery device 200 can be a guide wire.

Figure 3:
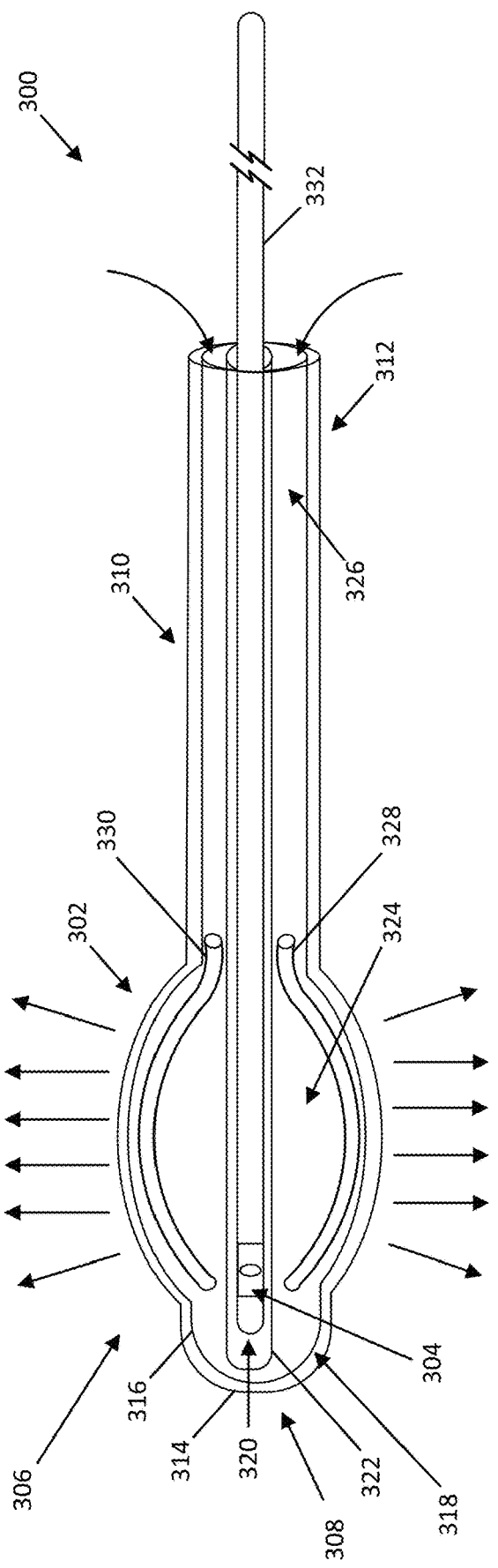
FIG. 3 illustrates generally an example of at least a portion of an apparatus that includes an expandable element and a plurality of lumens with an ultrasonic transducer disposed within one of the lumens.

FIG. 3 illustrates generally an example of at least a portion of an apparatus 300 that includes an expandable element 302 and a plurality of lumens with an ultrasonic transducer 304 disposed within one of the lumens. The apparatus 300 can comprise an elongate member 306 that includes the expandable element 302 at a distal end 308 of the apparatus 300 and an axial element 310 that includes a proximal end 312 of the elongate member 306. The elongate member 306 can have an outer surface 314 and an interior surface 316 that defines an outer wall region 318. The outer wall region 318 can include one or more polymeric materials. For example, the outer wall region 318 can comprise at least a silicone-containing material.

In addition, the elongate member 306 can include a central lumen 320 defined by a boundary surface 322. An interior region 324 can be disposed between the boundary surface 322 and the interior surface 316. The interior region 324 can have an expandable volume. For example, the interior region 324 can be filled with a fluid such that pressure is exerted by the fluid in the interior region 324 onto the interior surface 316 causing the volume of the interior region 324 to increase, which in turn results in the expansion of the expandable element 302. In the illustrative example of FIG. 3, the fluid disposed within the interior region 324 has not caused expansion of the expandable element 302. The fluid can be added to the interior region 324 via a channel 326 located in the axial element 310. In examples, the expandable region 302 can expand in a manner similar to that explained with respect to FIG. 1B, such that a volume of the interior region 324 increases in volume to at least 2 times an initial volume of the interior region 324, at least 3 times the initial volume of the interior region 324, at least 4 times the initial volume of the interior region 324, or at least 5 times the initial volume of the interior region 324.

In examples, both the central lumen 320 and the interior region 324 can be filled with a fluid. The central lumen 320 and the interior region 324 can be filled with a same fluid in various instances, while in other situations, the central lumen 320 and the interior region 324 can be filled with a different fluid. In illustrative examples, at least one of the central lumen 320 and the interior region 324 can be filled at least partially with an aqueous solution, such as water.

The elongate member 306 can also include a plurality of additional lumens, such as a first additional lumen 328 and a second additional lumen 330. In examples, a diameter of the central lumen 320 can be greater than a diameter of the first additional lumen 328 and a diameter of the second additional lumen 330. In various implementations, the first additional lumen 328 and the second additional lumen 330 can be formed from a material that is different from a material used to form the outer wall region 318. Additionally, the first additional lumen 328 and the second additional lumen 330 can be filled at least partially with a fluid that is different from the fluid located in at least one of the central lumen 320 or the interior region 324. In one or more examples, the first additional lumen 328 and the second additional lumen 330 can be at least partially filled with a same fluid.

The apparatus 300 can also include a second elongate member 332 that includes the ultrasonic transducer 304. The second elongate member 332 can be removably disposed within the central lumen 320. In examples, the second elongate member 332 can slide into and out of the central lumen 320. In one or more examples, the second elongate member 332 can also include a rotating drive shaft that enables transmission of acoustic energy radially by the ultrasonic transducer 304.

The elongate member 306 and the second elongate member 332 can have a number of lengths. In examples, a length of the elongate member 306 can be different from a length of the second elongate member 332. A length of the elongate member 306 can, in one or more examples, be from about 5 cm to about 30 cm, from about 7 cm to about 25 cm, or from about 10 cm to about 20 cm. A length of the second elongate member 332, in one or more examples, can be from about 10 cm to about 200 cm, from about 25 cm to about 150 cm, or from about 50 cm to about 125 cm.

Figure 4:
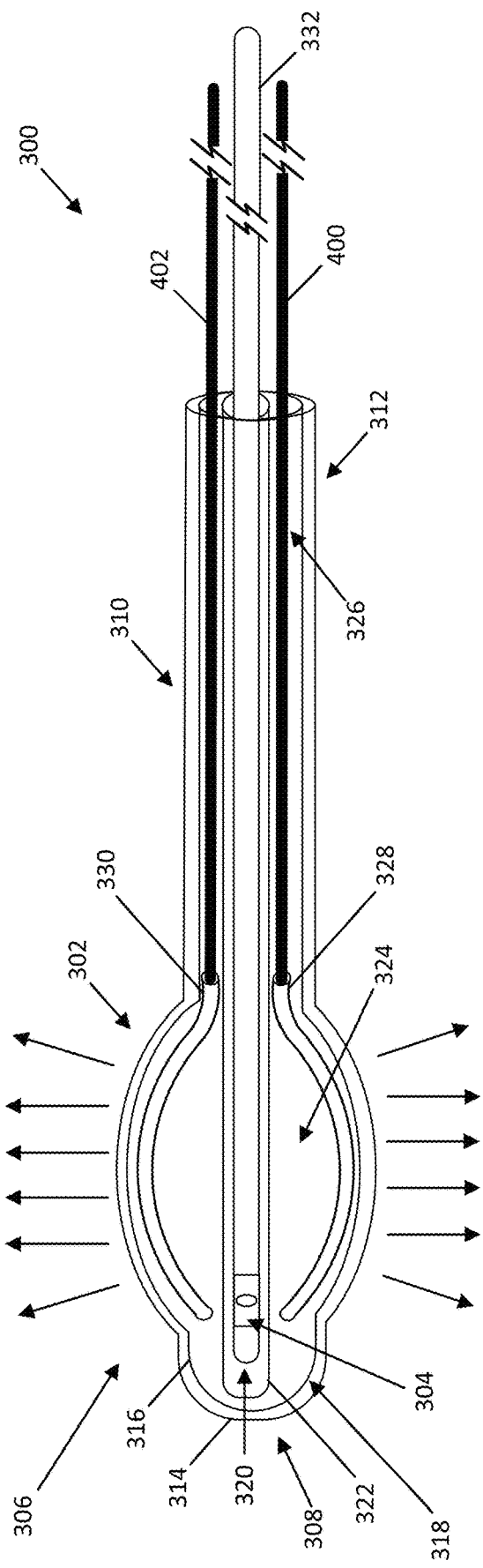
FIG. 4 illustrates generally an example of at least a portion of an apparatus that includes an expandable element and a plurality of lumens with an ultrasonic transducer disposed within one of the lumens and guide wires for radiation sources disposed within at least one of the other lumens.

FIG. 4 illustrates generally an example of at least a portion of the apparatus 300 that includes the expandable element 302 and a plurality of lumens with an ultrasonic transducer 304 disposed within one of the lumens and guide wires for radiation sources disposed within at least one of the other lumens. In examples, a first radiation source delivery device 400 can be disposed in the first additional lumen 328 and a second radiation source delivery device 402 can be disposed in the second additional lumen 330. The first radiation source delivery device 400 can be removably disposed within the first additional lumen 328 and the second radiation source delivery source 402 can be removably disposed within the second additional lumen 330. For example, the first radiation source delivery device 400 can slide into and out of the first additional lumen 328 and the second radiation source delivery device 402 can slide into and out of the second additional lumen 330. In illustrative examples, the radiation source delivery devices 400, 402 can be hollow and a radiation source can be placed within the interior of the radiation source delivery devices 400, 402. In additional examples, the radiation source delivery devices 400, 402 can include material that emits radiation to treat biological conditions, such as cancer.

Figure 5:
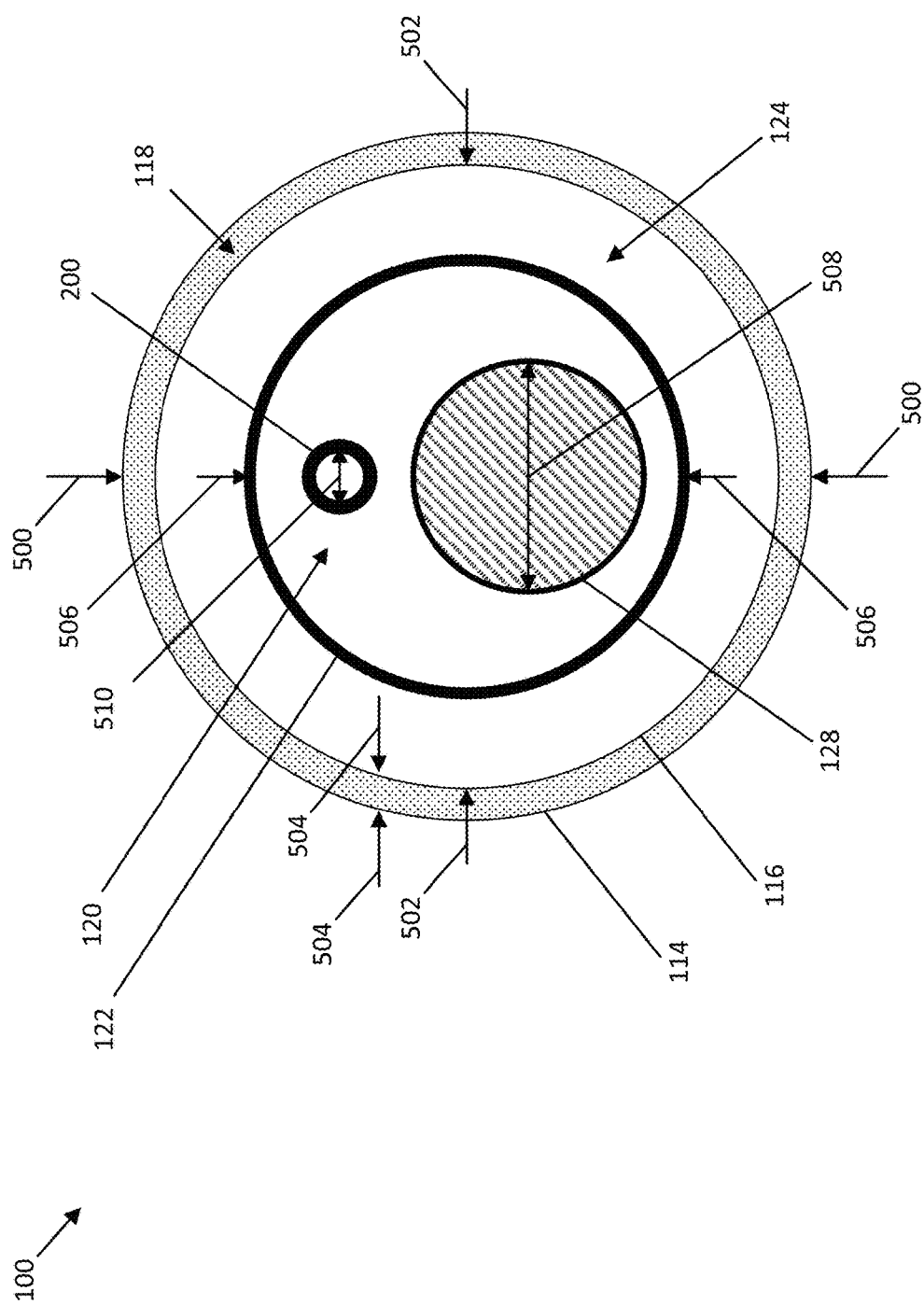
FIG. 5 illustrates generally a cross-sectional view of an example of at least a portion of a distal end of an apparatus that includes an ultrasonic transducer located within a lumen of the apparatus and a guide wire located within the lumen.

FIG. 5 illustrates generally a cross-sectional view of an example of at least a portion of the distal end 108 of the apparatus 100 that includes an ultrasonic transducer 104 located within a lumen 120 of the apparatus 100 and a radiation source delivery device 200 located within the lumen 120. In examples, the outer surface 114 can have a diameter shown by the arrows 500. The diameter of the outer surface 114, when the interior region 124 is not inflated, can be from about 5 mm to about 35 mm, from about 8 mm to about 30 mm, or from about 10 mm to about 25 mm. Additionally, the interior surface 116, when the interior region 124 is not inflated can have a diameter indicated by arrows 502 from about 8 mm to about 30 mm, from about 10 mm to about 25 mm, or from about 12 mm to about 20 mm. When the interior region 124 is inflated, the outer surface 114 can have a diameter from about 20 mm to about 100 mm, from about 25 mm to about 80 mm, or from about 30 mm to about 60 mm. In addition, when the interior region 124 is inflated, the interior surface 116 can have a diameter from about 15 mm to about 95 mm, from about 20 mm to about 85 mm, or from about 25 mm to about 75 mm.

A difference in the diameter of the outer surface 114 and the diameter of the interior surface 116 can define a thickness of the outer wall region 118 indicated by arrows 504. The thickness of the outer wall region 118 can be from about 0.05 mm to about 0.9 mm, from about 0.08 mm to about 0.6 mm, or from about 0.1 mm to about 0.5 mm. In one or more examples, the thickness of the outer wall region 118 can be no greater than about 0.5 mm, no greater than about 0.4 mm, no greater than about 0.3 mm, or no greater than about 0.2 mm. The thickness of the outer wall region 118 can be less than a thickness of a conventional applicator due to the interference that can result with respect to signals transmitted and received by the ultrasonic transducer 104 if the thickness of the outer wall region 118 is greater than a threshold thickness.

In illustrative examples, the lumen 120 can have a diameter indicated by the arrows 506 from about 0.5 mm to about 25 mm, from about 1 mm to about 20 mm, or from about 2 mm to about 15 mm. In additional examples, the second elongate member 128 can have a diameter indicated by 508 from about 0.1 mm to about 15 mm, from about 0.3 mm to about 10 mm, or from about 0.5 mm to about 5 mm. In one or more examples, the radiation source delivery device 200 can have a thickness indicated by 510 from about 0.05 mm to about 8 mm, from about 0.08 mm to about 5 mm, or from about 0.1 mm to about 3 mm.

Figure 6:
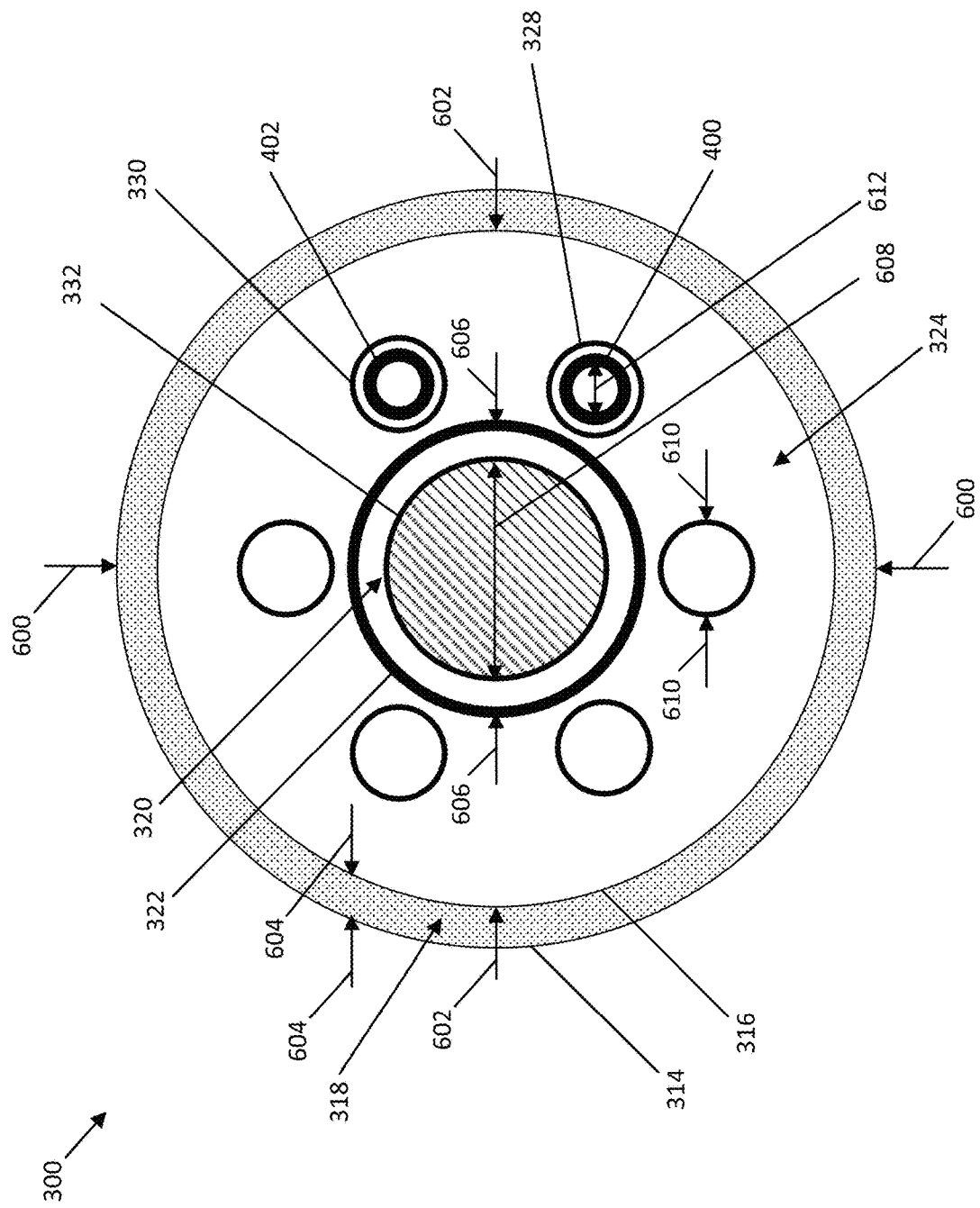
FIG. 6 illustrates generally a cross-sectional view of an example of at least a portion of a distal end of an apparatus that includes a plurality of lumens with an ultrasonic transducer located within one of the lumens and guides wires for radiation sources located within at least one of the other lumens.

FIG. 6 illustrates generally a cross-sectional view of an example of at least a portion of the distal end 306 of the apparatus 300 that includes a plurality of lumens with an ultrasonic transducer 304 located within one of the lumens and delivery devices for radiation sources located within at least one of the other lumens. In examples, the outer surface 314 can have a diameter shown by the arrows 600. The diameter of the outer surface 314, when the interior region 324 is not inflated, can be from about 5 mm to about 50 mm, from about 10 mm to about 40 mm, or from about 15 mm to about 30 mm. Additionally, the interior surface 316, when the interior region 324 is not inflated can have a diameter shown by arrows 602 from about 3 mm to about 40 mm, from about 5 mm to about 30 mm, or from about 10 mm to about 25 mm. When the interior region 324 is inflated, the outer surface 314 can have a diameter from about 20 mm to about 110 mm, from about 25 mm to about 90 mm, or from about 30 mm to about 65 mm. In addition, when the interior region 324 is inflated, the interior surface 316 can have a diameter from about 15 mm to about 100 mm, from about 20 mm to about 85 mm, or from about 25 mm to about 60 mm.

A difference in the diameter of the outer surface 314 and the diameter of the interior surface 316 can define a thickness of the outer wall region 318 indicated by arrows 604. The thickness of the outer wall region 318 can be from about 0.05 mm to about 0.5 mm, from about 0.08 mm to about 0.4 mm, or from about 0.1 mm to about 0.3 mm. In one or more examples, the thickness of the outer wall region 318 can be no greater than about 0.5 mm, no greater than about 0.4 mm, no greater than about 0.3 mm, or no greater than about 0.2 mm. The thickness of the outer wall region 318 can be less than a thickness of a conventional applicator due to the interference that can result with respect to signals transmitted and received by the ultrasonic transducer 304 if the thickness of the outer wall region 318 is greater than a threshold thickness.

In illustrative examples, the central lumen 320 can have a diameter indicated by the arrows 606 from about 0.5 mm to about 25 mm, from about 1 mm to about 20 mm, or from about 2 mm to about 15 mm. In additional examples, the second elongate member 332 can have a diameter indicated by 608 from about 0.1 mm to about 15 mm, from about 0.3 mm to about 10 mm, or from about 0.5 mm to about 5 mm. In one or more examples, the radiation source delivery device 400 can have a diameter indicated by 510 from about 0.05 mm to about 8 mm, from about 0.08 mm to about 5 mm, or from about 0.1 mm to about 3 mm. Although not shown in the illustrative example of FIG. 6, the radiation source delivery device 402 can also have a diameter from about 0.05 mm to about 8 mm, from about 0.08 mm to about 5 mm, or from about 0.1 mm to about 3 mm. Further, although the illustrative example of FIG. 6 indicates that the first additional lumen 328 and the second additional lumen 330 include radiation source delivery devices, such as guide wires, other additional lumen can also include guide wires in various examples.

Figure 7:
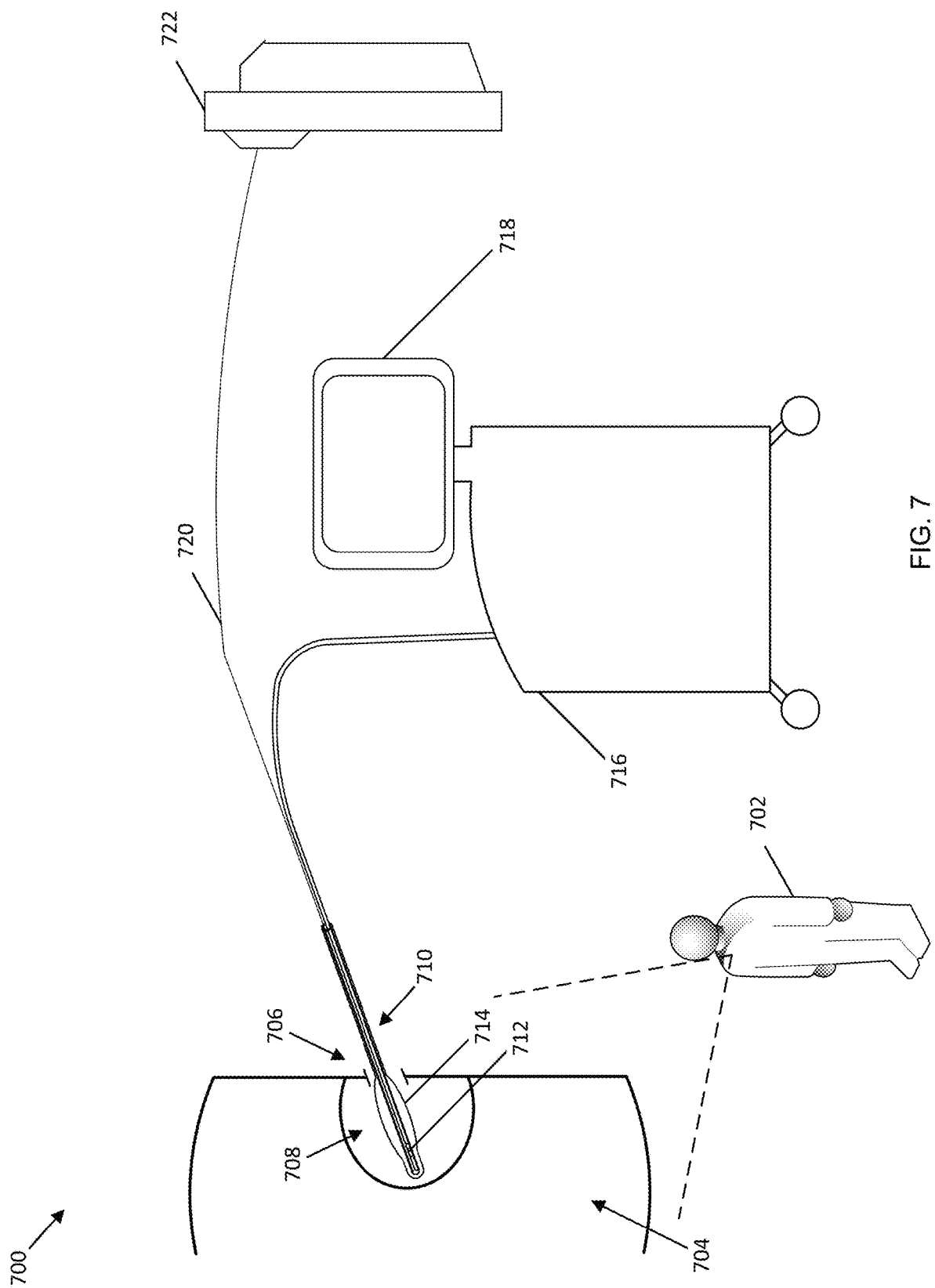
FIG. 7 illustrates generally an example of at least a portion of an environment where radiation therapy can be provided to a tissue region using an applicator that includes an expandable element and an ultrasonic transducer to produce images of the tissue region.

FIG. 7 illustrates generally an example of at least a portion of environment 700 where radiation therapy can be provided to a tissue region using an applicator that includes an expandable element and an ultrasonic transducer to produce images of the tissue region. The environment 700 includes a patient 702 and the illustrative example of FIG. 7 shows an expanded view of a tissue region 704 of the patient 702. In examples, the tissue region 704 can be located at various parts of the body of the patient. In illustrative examples, the tissue region 704 can be located on or near a breast of the patient 702.

An incision 706 has been made in the tissue region 704. The incision 706 can be made in the tissue region 704 initially to remove a tumor from the tissue region 704. Removal of the tumor from the tissue region 704 can produce a cavity 708 within the tissue region 704. An apparatus 710 can be inserted into the cavity 708 via the incision site 706. In examples, the apparatus 710 can be inserted into the cavity 708 within a threshold period of time after the tumor is removed, such as no greater than 12 hours after the tumor was removed, no greater than 8 hours after the tumor was removed, no greater than 4 hours after the tumor was removed, or no greater than 1 hour after the tumor was removed.

The apparatus 710 can include an ultrasonic transducer 712 and an expandable element 714. In examples, the ultrasonic transducer 712 can be located in a catheter that is coupled to an imaging apparatus 716 that includes a display 718. In addition, the expandable element 714 can be inflated to increase a volume of an interior region of the apparatus 710. In illustrative examples, the apparatus 710 can include the apparatus 100 of FIG. 1A, FIG. 1B, FIG. 2, and FIG. 5. In additional examples, the apparatus 710 can include the apparatus 300 of FIG. 3, FIG. 4, and FIG. 6.

The ultrasonic transducer 712 can emit acoustic energy and the ultrasonic transducer 712 can also receive signals indicating scattering or reflection of the acoustic energy. The signals transmitted and received by the ultrasonic transducer 712 can be sent to the imaging apparatus 716. The imaging apparatus 716 can process the signals from the ultrasonic transducer 716 to generate images that represent the cavity 708 and at least a portion of the apparatus 710. The images produced by the imaging apparatus 716 based on the signals obtained from the ultrasonic transducer 712 can be 2-dimensional (2D) images. In additional examples, the images produced by the imaging apparatus 716 based on the signals obtained from the ultrasonic transducer 712 can be 3-dimensional (3D) images.

The images generated by the imaging apparatus 716 can indicate features related to the tissue region 704. For example, the images generated by the imaging apparatus 716 can indicate a surface of the skin of the tissue region 704. In additional examples, the images generated by the imaging apparatus 716 can indicate bone within the tissue region 704 or adjacent to the tissue region 704. In further examples, the images generated by the imaging apparatus 716 can indicate voids or air gaps within the cavity 708, such as air gaps between the apparatus 710 and the inner surface of the cavity 708. In examples, the imaging apparatus 716 can compare the signals obtained from the ultrasonic transducer 712 to feature templates that indicate the presence of features that can be related to the tissue region 704. The imaging apparatus 716 can indicate a feature, such as bone, voids, or skin surface, in images based on at least a threshold amount of the signals obtained from the ultrasonic transducer 712 corresponding to a feature of a template. In illustrative examples, a template for air gaps can indicate a medium level tissue signal, followed by a bright reflection at air interface followed by a dark shadow.

The imaging apparatus 716 can implement speckle reduction techniques to produce images based on signals obtained from the ultrasonic transducer 712. In examples, speckle reduction can be performed using a low pass filter. In additional examples, speckle reduction can be performed using speckle reducing anisotropic diffusion (SRAD). In further examples, speckle reduction can be performed using elevation compounding techniques. The imaging apparatus 716 can also perform the enhancement of edge features to produce images based on the signals obtained from the ultrasonic transducer 712. For example, the imaging apparatus 716 can implement a Sobel edge filter to produce images based on signals obtained from the ultrasonic transducer 712. The imaging apparatus 716 can also use a high pass filter to enhance edge features to produce images based on signals obtained from the ultrasonic transducer 712.

The imaging apparatus 716 can also optimize at least one of brightness or contrast to produce images based on signals obtained from the ultrasonic transducer 712. In examples, brightness can be auto-adjusted using histogram equalization techniques. Depth gain compensation can also be utilized by the imaging apparatus 716 to optimize at least one of brightness or contrast in generating images based on signals obtained from the ultrasonic transducer 712.

Signals can be obtained by the imaging apparatus 716 from the ultrasonic transducer 712 to generate images when the apparatus 710 is inserted into the cavity 708 and before radiation is delivered to the tissue region 704. In addition, signals can be obtained by imaging apparatus 716 from the ultrasonic transducer 712 to generate images while radiation is being delivered to the tissue region 704. Further, signals can be obtained by the imaging apparatus 716 from the ultrasonic transducer 712 to generate images after a dose of radiation has been delivered to the tissue region 704.

The apparatus 710 can also include a guide wire 720 that is coupled to a radiation source 722. In examples, the radiation source apparatus 722 can include a high dose rate (HDR) afterloader. The radiation source apparatus 722 can cause radioactive materials to move along the guide wire 720 and into a portion of the guide wire 720 that is located in the cavity 708. In illustrative examples, the radiation source apparatus 722 can deliver radiation emitted from $^{192}$Ir or $^{60}$Co.

A dose of radiation delivered from the radiation source apparatus 722 to the tissue region 704 using the guide wire 720 can be determined based on signals obtained from the ultrasonic transducer 712. For example, signals obtained from the ultrasonic transducer 712 can be used to determine a volume of the cavity 708. Additionally, signals obtained from the ultrasonic transducer 712 can be used to determine a location of the apparatus 710 within the cavity 708 and a location of the guide wire 720 within the cavity 708. Based on at least one of a volume of the cavity 708 or a location of the guide wire 720 within the cavity 708, a radiation dose to be delivered to the tissue region 704 can be determined. In examples, the delivery of the radiation dose can include at least one of a time component, an intensity component, or a location component. The time component can include an amount of time that the tissue region 704 is exposed to radiation from a radiation source. The intensity component can indicate at least one of a type of radiation source used to deliver the radiation to the tissue region 704 or a number of radiation sources used to deliver the radiation to the tissue region 704. The location component can indicate where one or more radiation sources are to be located along the guide wire 720 and/or locations of additional radiation sources located along additional guide wires (not shown in FIG. 7) included in the apparatus 710 and coupled to the radiation source apparatus 722.

The dose of radiation delivered to the tissue region 704 can be delivered over a period of time. For example, a dose of radiation can be delivered to the tissue region for a period of time from about 15 minutes to about 90 minutes, from about 20 minutes to about 75 minutes or from about 25 minutes to about 40 minutes. Additionally, a dose of radiation delivered by one or more radiation sources to the tissue region 704 can be from about 15 grays to about 30 grays or from about 18 grays to about 25 grays at a surface of the apparatus 710. Further, a dose of radiation delivered by one or more radiation sources to the tissue region 704 can be from about 6 grays to about 20 grays or from about 9 grays to about 14 grays to about 1 cm from the inner surface of the cavity 708.

Figure 8:
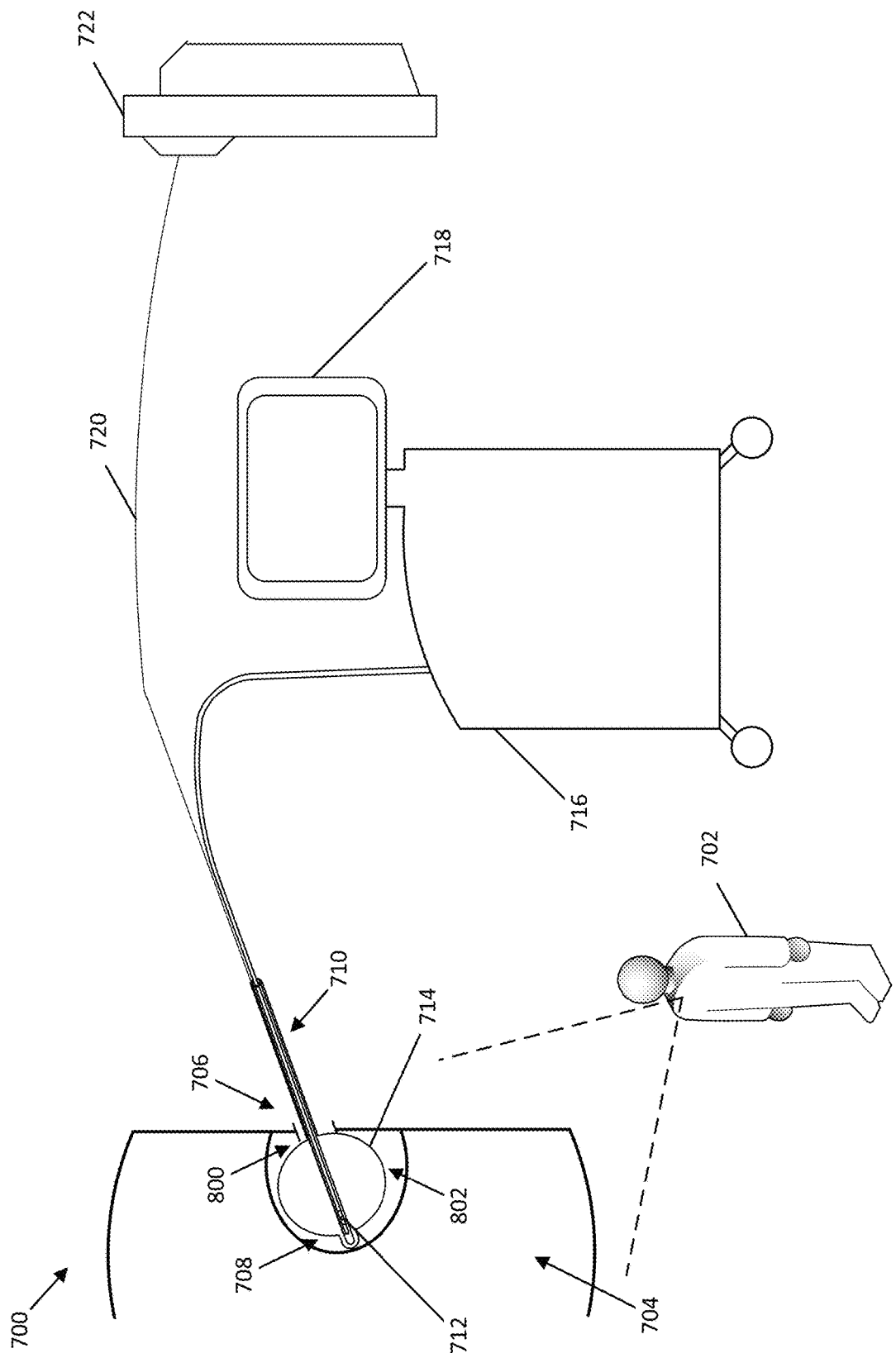
FIG. 8 illustrates generally an example of at least a portion of an environment where radiation therapy can be provided to a tissue region using an applicator with an expandable element that has been inflated and the applicator includes an ultrasonic transducer to produce images of the tissue region.

FIG. 8 illustrates generally an example of at least a portion of the environment 700 where radiation therapy can be provided to a tissue region using an applicator with an expandable element that has been inflated and an ultrasonic transducer to produce images of the tissue region. In the illustrative example of FIG. 8, the expandable element 714 of the apparatus 710 has been inflated and occupies a greater volume of the cavity 708 than in FIG. 7. FIG. 8 also indicates air gaps 800 and 802 between the inflated expandable element 714 and the inner surface of the cavity 708. In examples, the imaging apparatus 716 can generate images indicating the air gaps 800 and 802.

Figure 9:
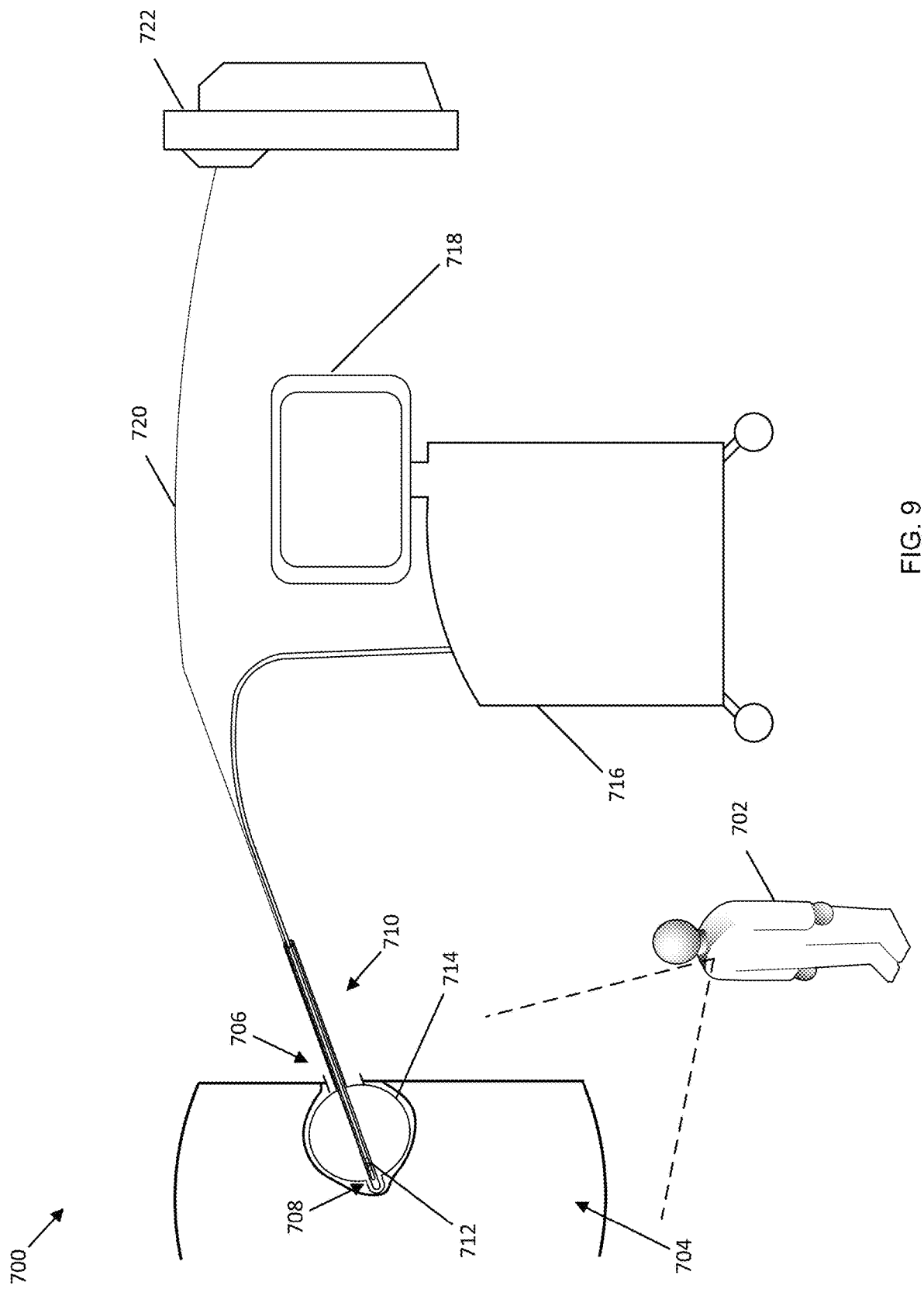
FIG. 9 illustrates generally an example of at least a portion of an environment where radiation therapy can be provided to a tissue region using an applicator that includes an expandable element and an ultrasonic transducer to produce images of the tissue region, where a shape of the tissue region conforms closely with an inflated expandable element.

FIG. 9 illustrates generally an example of at least a portion of the environment 700 where radiation therapy can be provided to a tissue region using an applicator that includes an expandable element and an ultrasonic transducer to produce images of the tissue region, where a shape of the tissue region conforms closely with an inflated expandable element. In the illustrative example of FIG. 9, the inner surface of the cavity 708 has been adjusted to conform more closely to the shape of the expandable element 714. In examples, vacuum ports of the apparatus 710 can be operated to remove air from the cavity 708 and cause the shape of the cavity 708 to more closely conform to the shape of the expandable element 714. In additional examples, a clinician can manipulate portions of the tissue region 704 to cause the shape of the cavity 708 to conform more closely to the shape of the expandable element 714. In illustrative instances, the shape of the cavity 708 can be modified to conform to the shape of the expandable element 714 in response to images showing air gaps within the cavity 708 between the inner surface of the cavity 708 and the surface of the apparatus 710 located within the cavity 708.

Figure 10:
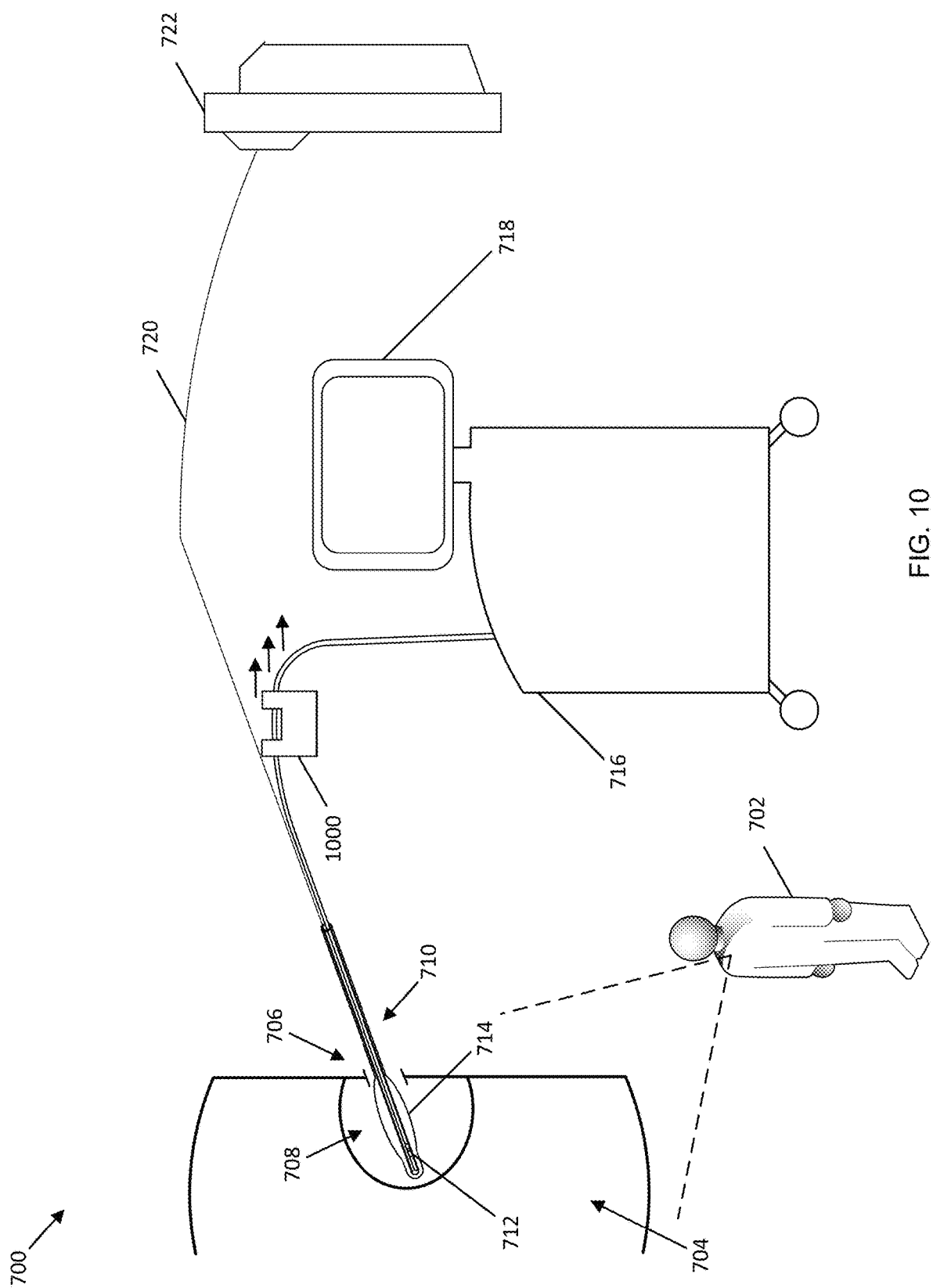
FIG. 10 illustrates generally an example of at least a portion of an environment where radiation therapy can be provided to a tissue region using an applicator that includes an expandable element and an ultrasonic transducer to produce images of the tissue region and the environment includes a stepper motor to move the ultrasonic transducer in an axial direction.

FIG. 10 illustrates generally an example of at least a portion of environment 700 where radiation therapy can be provided to a tissue region using an applicator that includes an expandable element and an ultrasonic transducer to produce images of the tissue region and the environment includes a stepper device 1000 to move the ultrasonic transducer in an axial direction. The axial direction can be along an axis defined longitudinally along the apparatus 710. In examples, the stepper device 1000 can move the ultrasonic transducer 714 axially in increments. For example, the stepper device 1000 can move the ultrasonic transducer 714 in about 1 mm increments in an axial direction with respect to an axis along which the apparatus 710 is disposed. In illustrative examples, the stepper device 1000 can move the ultrasonic transducer 714 in increments over a period of time. To illustrate, the stepper device 1000 can move the ultrasonic transducer 714 at a rate of about 1 mm/second for a total of about 10 seconds or for a total of about 15 seconds.

As the ultrasonic transducer 712 is moved by the stepper device 1000 in an axial direction, the imaging apparatus 716 can obtain signals from the ultrasonic transducer 712. The signals obtained from the ultrasonic transducer 712 can be used by the imaging apparatus 716 to generate 2D cross-sectional images. The 2D cross-sectional images can be processed by the imaging apparatus 716 to produce 3D images that represent the cavity 708 and features proximate to the cavity 708.

Figure 11:
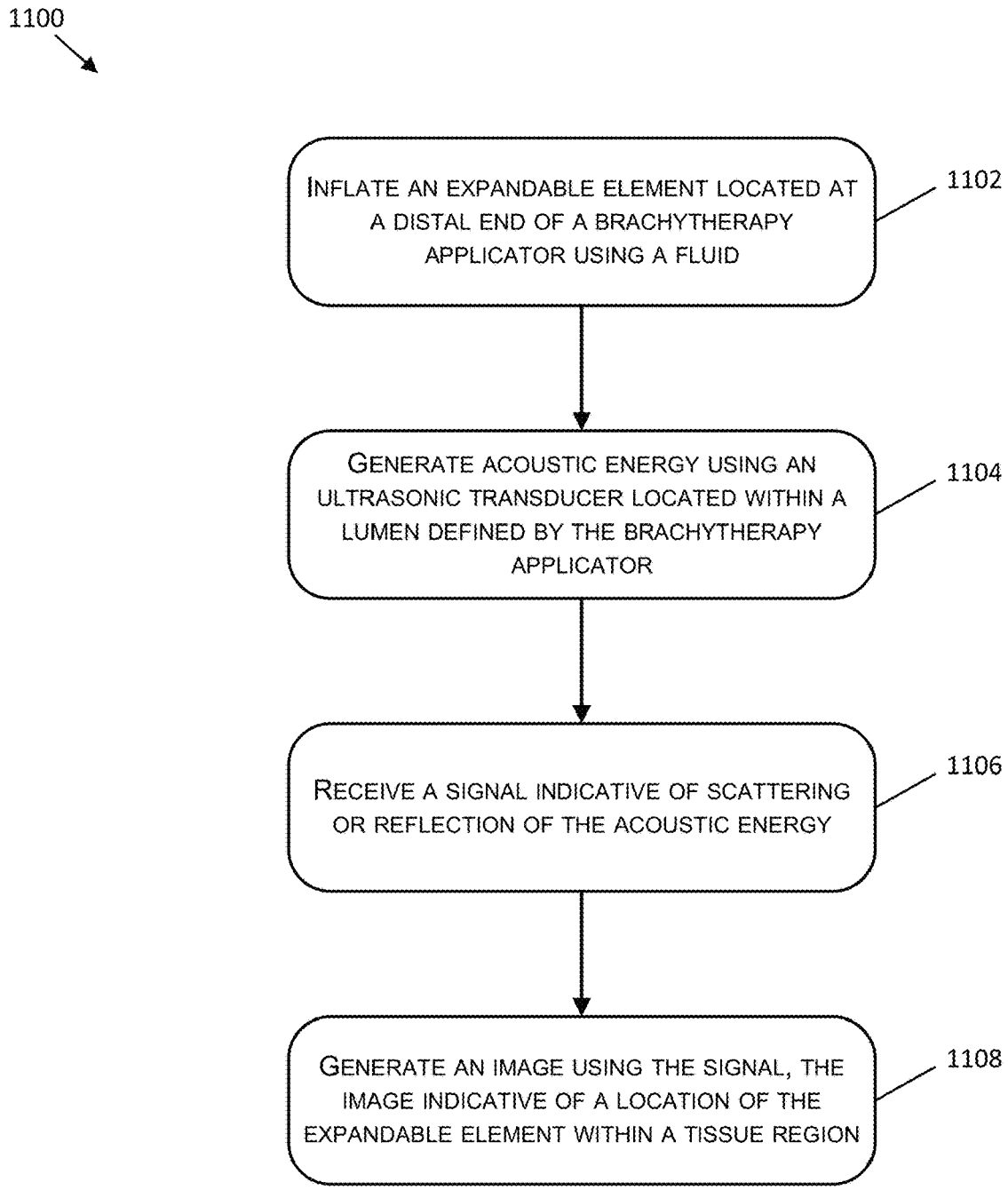
FIG. 11 illustrates generally an example of at least a portion of a method to generate images of a tissue region using an applicator that includes an expandable element and an ultrasonic transducer.

FIG. 11 illustrates generally an example of at least a portion of method 1100 to generate images of a tissue region using an applicator that includes an expandable element and an ultrasonic transducer. At 1102, the method 1100 includes inflating an expandable element located at a distal end of a brachytherapy application using a fluid. In examples, the brachytherapy applicator can be located with a cavity of a tissue region of a patient. The fluid can include water, a saline solution, or another liquid suitable for transmitting and receiving ultrasonic energy.

At 1104, the method 1100 includes generating acoustic energy using an ultrasonic transducer located within a lumen defined by the brachytherapy applicator. In various examples, the ultrasonic transducer can be included in a catheter that is located within the lumen defined by the brachytherapy application. The brachytherapy applicator can include a single lumen in particular examples. Additionally, in other instances, the brachytherapy applicator can include multiple lumens.

At 1106, the method 1100 includes receiving a signal indicative of scattering or reflection of the acoustic energy. In examples, the signal can be received by an apparatus that generates images using signals related to acoustic energy. At 1108, the method 1100 includes generating an image using the signal. The image can be indicative of a location of the expandable element within a tissue region. In various situations, the image can indicate air gaps within a cavity of the tissue region and a technician can modify a shape of the cavity to more closely conform to a shape of the applicator. In one or more examples, the images generated using the signals of the ultrasonic transducer can visually highlight one or more features related to the tissue region. For example, images can be generated that visually highlight at least one of bone proximate to the tissue region, a surface of the skin that defines an outer portion of a cavity within the tissue region, or one or more air gaps included in the cavity.

Figure 12:
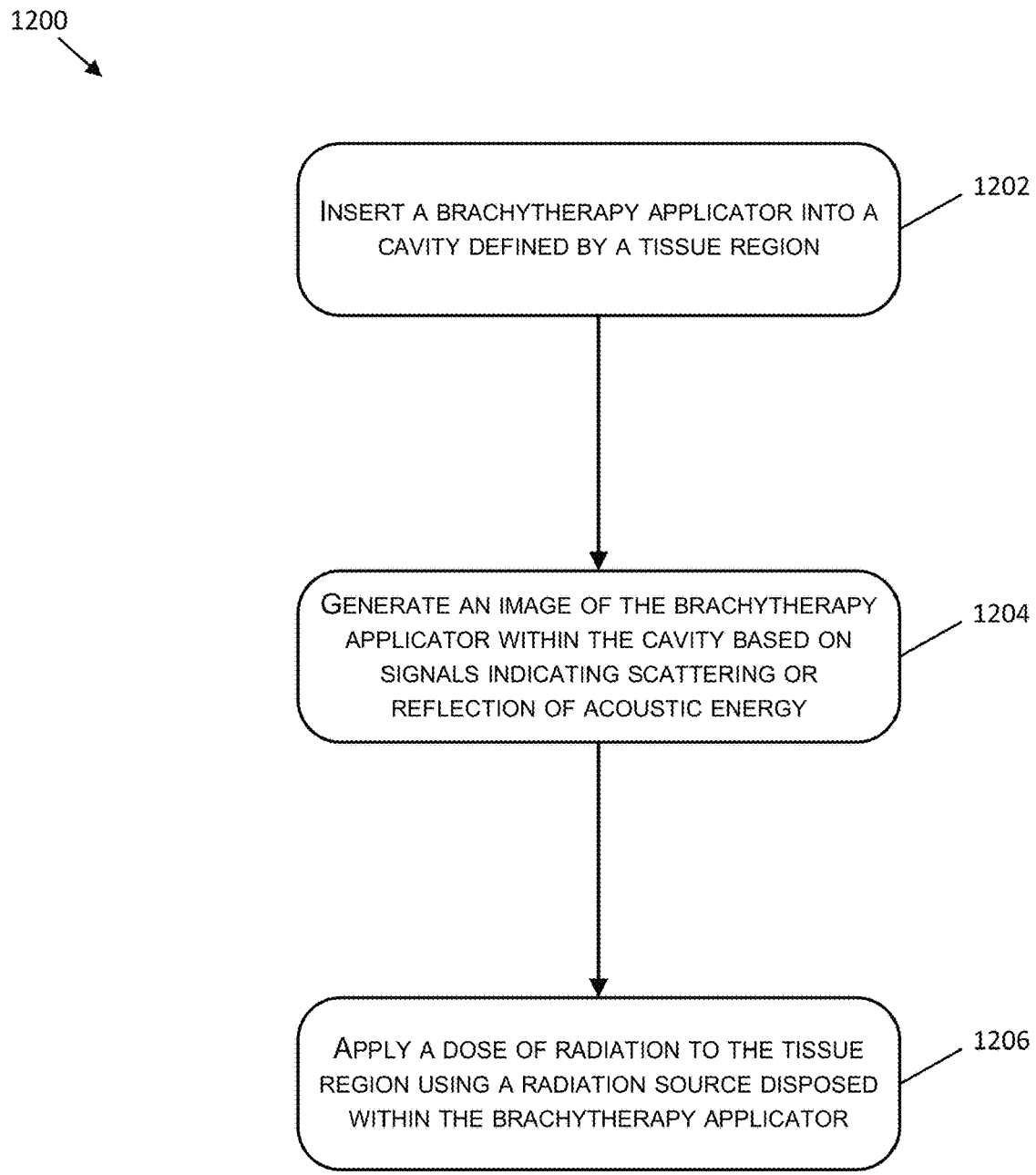
FIG. 12 illustrates generally an example of at least a portion of a method to apply radiation to a tissue region using an applicator that includes an ultrasonic transducer.

FIG. 12 illustrates generally an example of at least a portion of a method 1200 to apply radiation to a tissue region using an applicator that includes an ultrasonic transducer. At 1202, the method 1200 includes inserting a brachytherapy applicator into a cavity device by a tissue region. In examples, the cavity can be created due to removal of a tumor from a patient. In illustrative examples, the cavity can be caused by removal of a tumor from a breast of a patient.

At 1204 the method 1200 includes generating an image of the brachytherapy applicator within the cavity based on signals indicating scattering or reflection of acoustic energy. The image can indicate features related to the cavity and the tissue region. For example, the image can indicate bone that is located proximate to the tissue region. The image can also indicate the surface of the skin near the tissue region. In addition, the image can indicate air gaps within the cavity between the applicator and an inner surface of the cavity. The acoustic energy can be transmitted and received by an ultrasonic transducer located within the brachytherapy applicator.

At 1206, the method 1200 includes applying a dose of radiation to the tissue region using a radiation source disposed within the brachytherapy application. For example, the brachytherapy applicator can include at least one guide wire that can be used to a move a radiation source into the cavity. In addition to the radiation dose being used to treat cancer related to the tissue region, ultrasonic energy can also be used therapeutically. That is, the ultrasonic transducer can be used to deliver a dose of acoustic energy to the tissue region. In examples, the ultrasonic transducer can operate in a first mode and transmit acoustic energy having a first range of wavelengths that are suitable for imaging. In one or more examples, the ultrasonic transducer can operate in a second mode and transmit acoustic energy having a second range of wavelengths that are suitable for treatment of one or more conditions, such as cancer.

The dose of radiation applied to the tissue region can be determined based on information derived from images produced using signals of the ultrasonic transducer. For example, a volume of a cavity to which radiation will be applied or to which radiation is being applied can be determined. In examples, a location of the brachytherapy applicator within the cavity can be determined. The dose of radiation applied to the tissue region can be determined based on at least one of the volume of the cavity or the location of the brachytherapy applicator.

Although the methods 1100 and 1200 have been described using images produced using ultrasound techniques, other techniques can be used to produce the images in other implementations, such as CT, PET, or MR.

Figure 13:
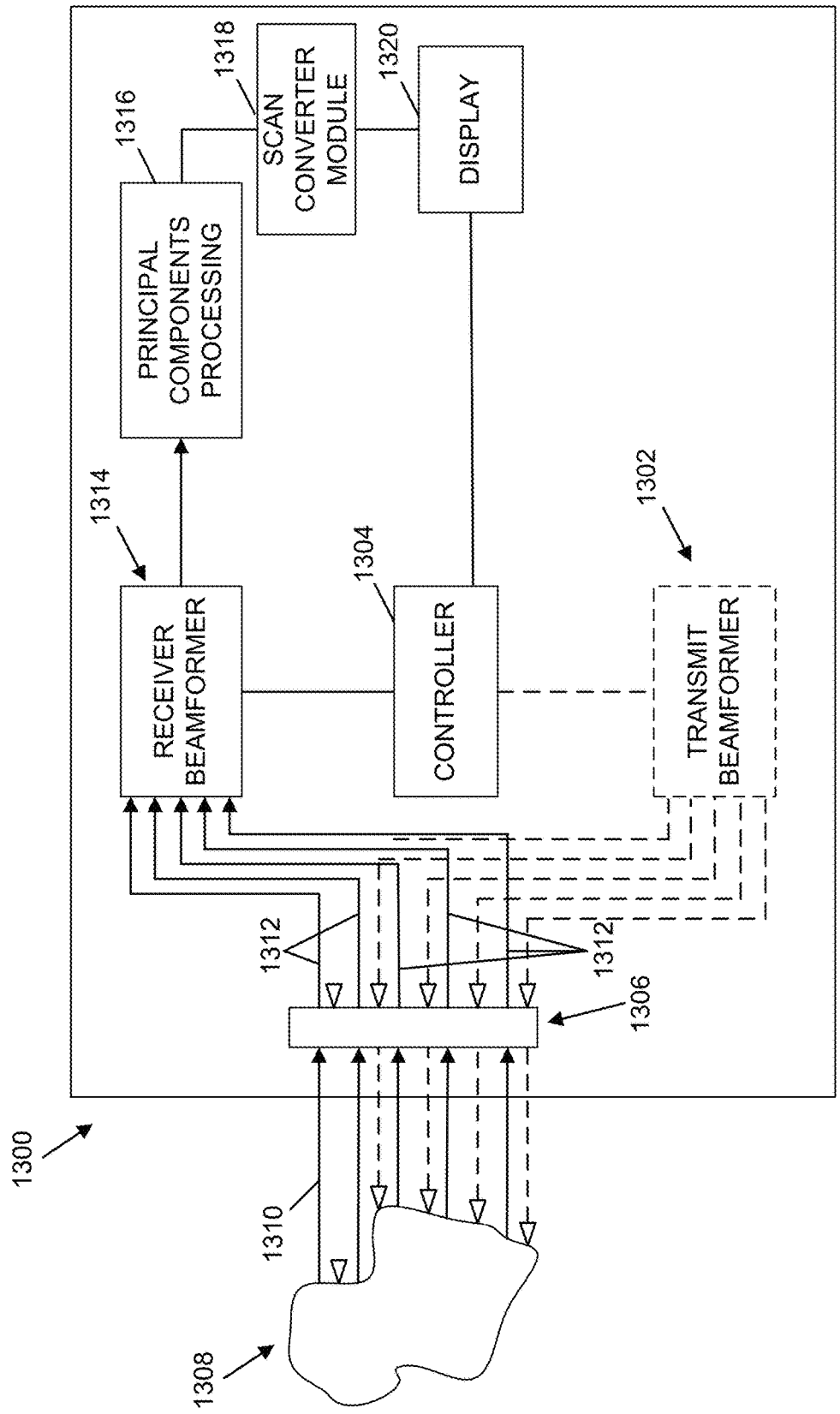
FIG. 13 illustrates generally an example of at least a portion of an ultrasound system that can be used to produce images according to implementations described herein.

FIG. 13 illustrates generally an example of at least a portion of an ultrasound system 1300 that can be used to produce images according to implementations described herein. The ultrasound system 1300 may optionally include a transmit beamformer 1302 which may include input thereto by controller 1304 to send electrical instructions to an array of transducers 1306 as to the specifics of the ultrasonic waves to be emitted by array 1306. Alternatively, system 1300 may be a receive only system and the emitted waves may be directed to the object 1308 from an external source.

In either case, echoes 1310 reflected by the object 1308 (and surrounding environment) are received by array 1306 and converted to electrical (e.g., radio frequency (RF)) signals 1312 that are input to receiver beamformer 1314. Controller 1304 may be external of the receiver beamformer 1314, as shown, or integrated therewith. Controller 1304 automatically and dynamically changes the distances at which scan lines are performed (when a transmit beamformer 1302 is included) and automatically and dynamically controls the receive beamformer 1314 to receive signal data for scan lines at predetermined distances. Distance/depth is typically calculated assuming a constant speed of sound in tissue (e.g., 1540 m/s or as desired or required) and then time of flight is recorded such that the returning echoes have a known origination. The summed RF lines output by the receiver beamformer 1314 are input to a principal components processing module 1316, which may be separate from and controlled by, or incorporated in controller 1304. Principal components module 1316 processes the signals obtained by the receiver beamformer 1314 and assembles them into an output signal.

The assembled output may be input into a scan converter module 1318. The image formed within the scan converter 1318 is displayed on display 1320. Although FIG. 13 has been described as an ultrasound system, it is noted that transducers 1306 may alternatively be transducers for converting electrical energy to forms of energy other than ultrasound and vice versa, including, but not limited to radio waves (e.g., where system 1300 is configured for RADAR), visible light, infrared, ultraviolet, and/or other forms of sonic energy waves, or some other arbitrary signal of arbitrary dimensions greater than one (such as, for example, a signal that is emitted by a target).

Figure 14:
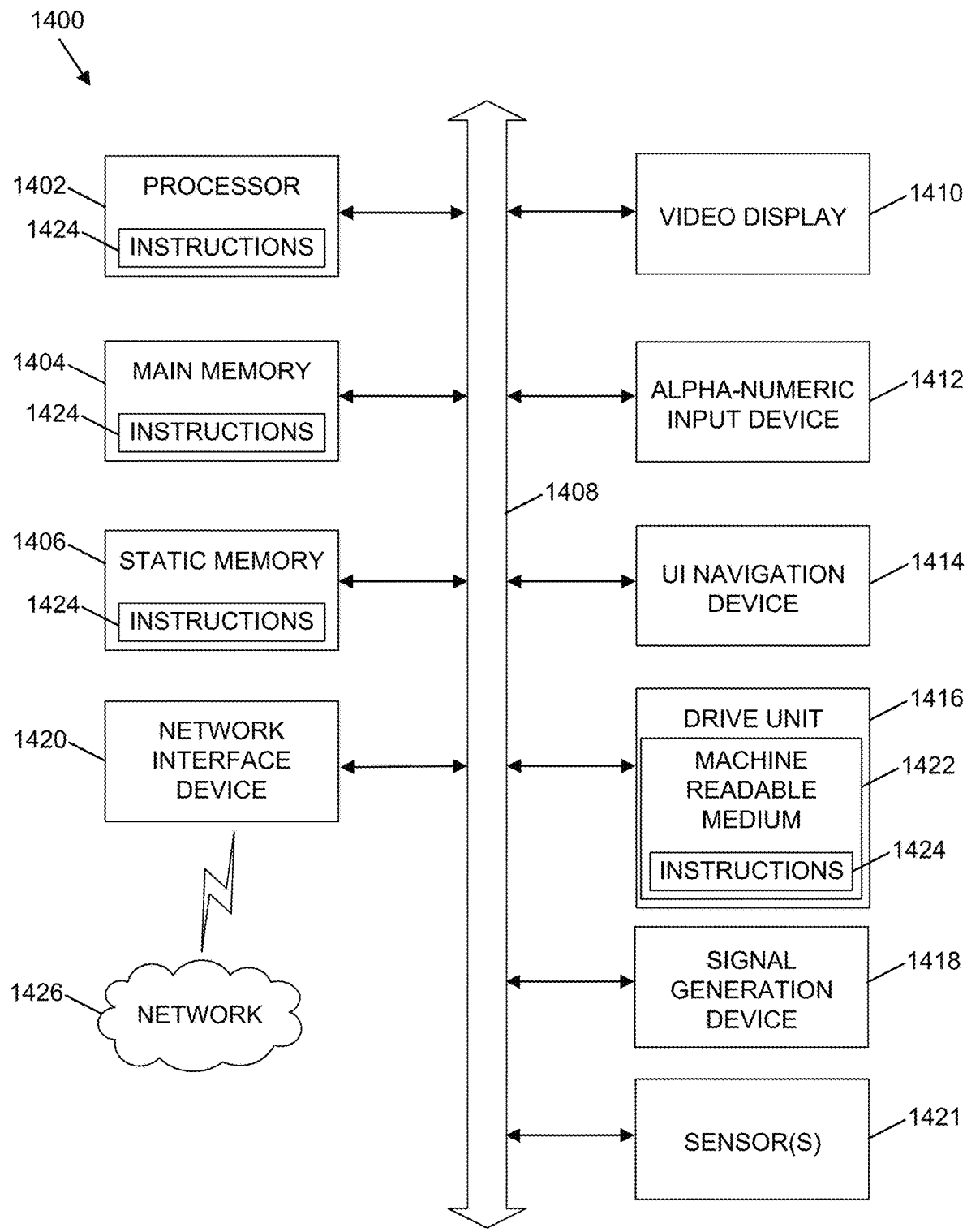
FIG. 14 illustrates generally an example of at least a portion of a computing device upon which one or more aspects of examples described herein can be implemented.

FIG. 14 illustrates generally an example of at least a portion of a computing device 1400 upon which one or more aspects of implementations described herein can be implemented.

Examples of computing device 1400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., computing device 1400) and software architectures that can be deployed in example embodiments.

In an example, the computing device 1400 can operate as a standalone device or the computing device 1400 can be connected (e.g., networked) to other machines.

In a networked deployment, the computing device 1400 can operate in the capacity of either a server or a client machine in server-client network environments. In an example, computing device 1400 can act as a peer machine in peer-to-peer (or other distributed) network environments. The computing device 1400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the computing device 1400. Further, while only a single computing device 1400 is illustrated, the term "computing device" shall also be taken to include any collection of machines that individually or jointly execute a set (or multiple sets) of instructions to perform any one or more of the methodologies discussed herein.

Example computing device 1400 can include a processor 1402 (e.g., a central processing unit (CPU), a graphics processing unit (GPU) or both), a main memory 1404 and a static memory 1406, some or all of which can communicate with each other via a bus 1408. The computing device 1400 can further include a display unit 1410, an alphanumeric input device 1412 (e.g., a keyboard), and a user interface (UI) navigation device 1414 (e.g., a mouse). In an example, the display unit 1410, input device 1412 and UI navigation device 1414 can be a touch screen display. The computing device 1400 can additionally include a storage device (e.g., drive unit) 1416, a signal generation device 1418 (e.g., a speaker), a network interface device 1420, and one or more sensors 1421, such as a global positioning system (GPS) sensor, compass, accelerometer, or other sensor.

The storage device 1416 can include a machine readable medium 1422 on which is stored one or more sets of data structures or instructions 1424 (e.g., software) embodying or utilized by any one or more of the methodologies or functions described herein. The instructions 1424 can also reside, completely or at least partially, within the main memory 1404, within static memory 1406, or within the processor 1402 during execution thereof by the computing device 1400. In an example, one or any combination of the processor 1402, the main memory 1404, the static memory 1406, or the storage device 1416 can constitute machine readable media.

While the machine readable medium 1422 is illustrated as a single medium, the term "machine readable medium" can include a single medium or multiple media (e.g., a centralized or distributed database, and/or associated caches and servers) that configured to store the one or more instructions 1424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1424 can further be transmitted or received over a communications network 1426 using a transmission medium via the network interface device 1420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

The concept of developing and applying an ultrasound-based system for breast IORT with HDR brachytherapy would make it possible for other centers to implement breast IORT with HDR brachytherapy; and may be implemented and utilized with the related processors, networks, and computer systems.

Experimental Example

The UVA breast team conducted a dosimetric study to establish that their image-guided breast IORT would improve RT dosimetry over conventional breast IORT. This study used CT scans from 14 patients previously treated at our institution with multi-lumen, balloon catheter based HDR brachytherapy (APBI). We performed comparison treatment plans for each of the 14 cases, by simulating the specifications of a 50 kV x-ray system for conventional Breast IORT and developing a volume-optimized HDR brachytherapy plan. Uniform volume optimization and prescription doses were used to permit direct comparisons between the two sample IORT plans. The HDR brachytherapy plans were superior or similar to the 50 kV superficial photon plans for conventional breast IORT in all dosimetric parameters (Table 1), with the exception of slightly higher heart dose that was still reasonably low, and did a better job of covering the entire volume of breast at high risk for cancer recurrence. Image-guided HDR intraoperative brachytherapy with a multi-lumen balloon applicator provides superior target volume coverage compared with 50 kV photons for conventional breast IORT, while maintaining doses within tolerance limits for normal tissues, including the heart and ribs.

TABLE 1

Dosimetric comparison of intraoperative radiation therapy plans between high dose rate (HDR) brachytherapy using multilumen/multidwell balloon catheter and superficial photon-based approach used in the TARGIT-A trial.

| Dose-Volume Parameter | Multilumen-Multidwell Balloon HDR Brachytherapy (mean (SD)]# | Superficial Photon Intraoperative Plan [mean (SD)]# | p value* |
|---|---|---|---|
| PTV_Eval | | | |
| V100 (%) | 88.2 (1.9) | 80.1 (2.0) | <0.001 |
| V150 (%) | 32.0 (2.4) | 39.2 (2.4) | <0.001 |
| V200 (%) | 7.9 (1.7) | 17.1 (3.1) | <0.001 |
| Balloon Surface Dose | | | |
| D99 (Gy) | 14.9 (1.3) | 15.6 (2.2) | 0.16 |
| Ipsilateral Breast DHI | 0.66 (0.03) | 0.53 (0.04) | <0.001 |
| Max Skin Dose (%) | 118.1 (55.5) | 133.0 (87.5) | 0.25 |
| Mean Heart Dose (Gy) (n = 8 left-sided tumors) | 0.32 (0.09) Range: 0.18-0.47 | 0.06 (0.02) Range: 0.04-0.09 | <0.001 |
| Max Rib Dose (%) | 70.8 (37.2) | 62.3 (43.9) | 0.34 |

DHI = dose homogeneity index;
DHI = (V100 − V150)/V100
*Statistical comparisons performed using two-tailed t-test, with significance assumed to be $p < 0.05$.
All related values based on 10 Gy prescription dose to permit ready comparisons.

The dosimetric results shown in Table 1 are predictable based upon the Ir-192 HDR brachytherapy source, which produces higher energy photons than used in conventional breast IORT with superficial photon systems, as well as the use of an applicator with multiple channels and multiple dwell positions per channel that permits volume optimization of radiation plans. The advantages of IORT with HDR brachytherapy versus the superficial photons of conventional breast IORT are well represented by the improved dose homogeneity index (DHI), as shown in Table 1. DHI is calculated by the formula [(V100−V150)/V100] and essentially represents the "smoothness" of a radiation plans, with higher DHI having a smaller volume of hotspots.

The better DHI provides the opportunity to deliver a higher dose to 1 cm beyond the applicator surface with HDR brachytherapy (12.5 Gy versus 5-7 Gy in conventional breast IORT) while maintaining the same applicator surface dose (~20 Gy) as in superficial photons. In our dosimetric study, we identified 12.5 Gy at 1 cm from the applicator as the recommended prescription dose for HDR brachytherapy breast IORT, based on seeking the highest dose that permitted 20 Gy surface dose to match that of conventional breast IORT with superficial photons. Therefore, we used 12.5 Gy for the prescription dose for UVA's image-guided breast IORT program. This dose is compared to other breast RT approaches in Table 2. Not the higher biological equivalent dose (BED) compared to TARGIT-A-style conventional breast IORT.

TABLE 2

Comparison of biological equivalent dose (BED) values for acute
and late effects for representative dose-fractionation schedules
for breast radiation therapy. Doses are scaled to represent dose delivered
to the PTV_Eval, which represents the lumpectomy cavity plus
1 cm with, with exclusion of the chest wall and skin. Supporting
citations provided. BED calculations were performed using TDFCalc
Version 1.04 (EyePhysics, LLC).

| Schedule Description | Dose (Fractionation) | $BED_{10\,Gy}$ (Gy) (Acute Effects) | $BED_{3\,Gy}$ (Gy) (Late Effects) |
|---|---|---|---|
| Conventional (WBI) | 60 Gy (30 fx) | 72.0 | 100.0 |
| ELIOT IORT trial | 21 Gy (1 fx) | 65.1 | 168.0 |
| Whelan et al. (WBI) | 42.5 Gy (16 fx) | 53.8 | 80.1 |
| NSABP B-39 APBI | 34 Gy (10 fx) | 45.6 | 72.5 |
| "Overnight" trial of APBI | 21 Gy (2 fx) | 43.0 | 94.5 |
| UVA HDR IORT dose | 12.5 Gy (1 fx) | 28.1 | 64.5 |
| TARGIT IORT trial | 5-7 Gy (1 fx) | 7.5-11.9 | 13.3-23.3 |

Abbreviations:
WBI, whole breast irradiation;
ABPI, accelerated partial breast irradiation;
IORT, intraoperative radiation therapy;
HDR, high dose rate brachytherapy;
fx, fraction;
NSABP, National Surgical Adjuvant Breast and Bowel Project;
ELIOT, intraoperative radiation therapy with electrons;
TARGIT, targeted intraoperative radiotherapy.

Figure 15A:
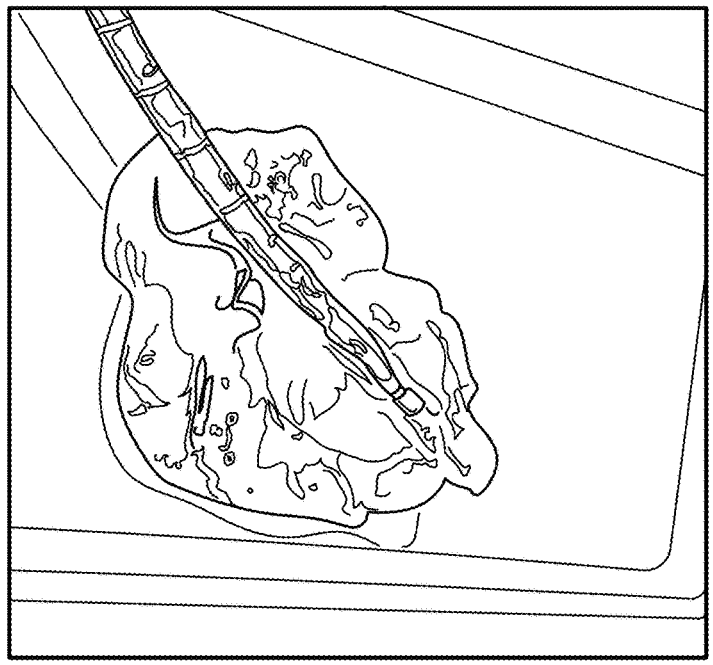
FIG. 15A illustrates a brachytherapy applicator with an extendable element and an ultrasonic transducer where the extendable element has been inflated and placed inside a simulated tissue region.

FIG. 15A illustrates a brachytherapy application with an extendable element and an ultrasonic transducer where the extendable element has been inflated and placed inside a simulated tissue region.

Figure 15B:
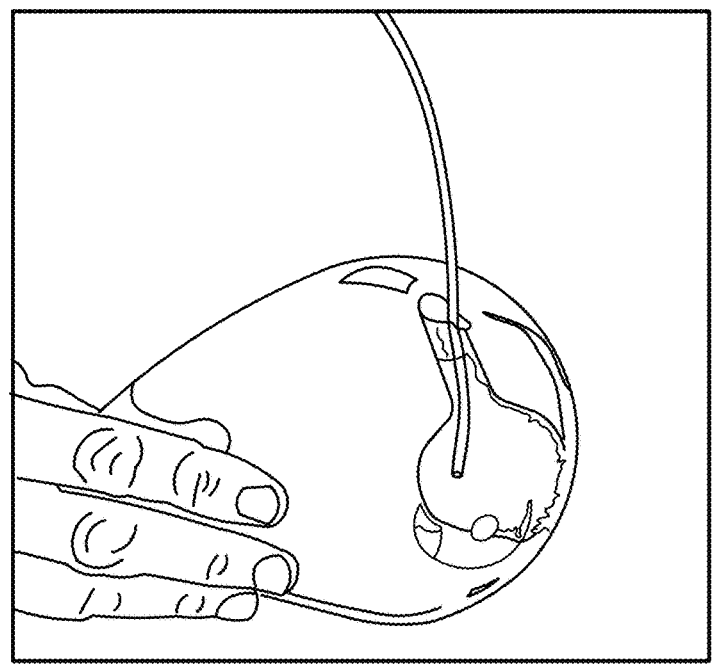
FIG. 15B illustrates a catheter including an ultrasonic transducer that has been placed inside a cavity of a simulated tissue region.

FIG. 15B illustrates a catheter including an ultrasonic transducer that has been placed inside a cavity of a simulated tissue region.

Figure 16A:
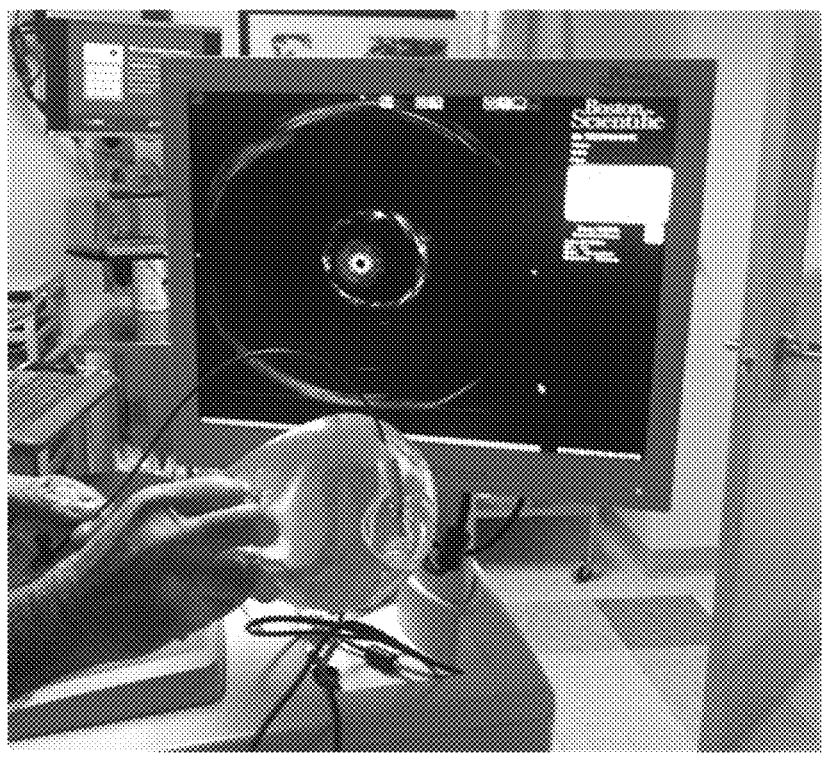
FIG. 16A illustrates an image produced using signals from an ultrasonic transducer located within a cavity of a simulated tissue region.

FIG. 16A illustrates an image produced using signals from an ultrasonic transducer located within a cavity of a simulated tissue region.

Figure 16B:
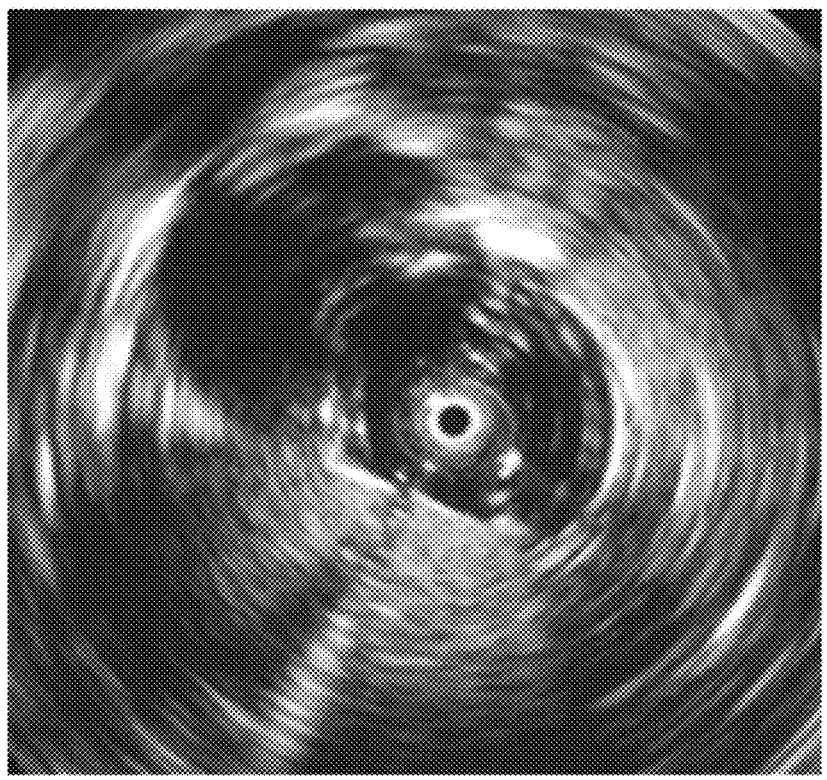
FIG. 16B illustrates a close up view of a portion of an image produced from an ultrasonic transducer located within a cavity of a simulated tissue region.

FIG. 16B illustrates a close up view of a portion of an image produced from an ultrasonic transducer located within a cavity of a simulate tissue region.

Various Notes & Examples

Example 1 can include or use subject matter (such as an apparatus, a method, a means for performing acts, or a device readable medium including instructions that, when performed by the device, can cause the device to perform acts), such as can include or use an apparatus, comprising a first elongate member defining a first lumen having an opening at a proximal end of the elongate member, an expandable element located at a distal end of the first elongate member; and an ultrasonic transducer located within the first lumen and positionable along the first elongate member.

Example 2 can include, or can optionally be combined with the subject matter of Example 1, to optionally include a radiation source delivery device located within the first lumen and positionable along the first elongate member.

Example 3 can include, or can optionally be combined with the subject matter of Examples 1 or 2, to optionally include the elongate member including a second lumen and a radiation source delivery device is located within the second lumen.

Example 4 can include, or can optionally be combined with the subject matter of Examples 1 through 3, to optionally include a stepper device coupled to the ultrasonic transducer, the stepper device being configured to move the ultrasonic transducer in specified increments along an axis defined longitudinally along the lumen and is located within the first elongate member.

Example 5 can include, or can optionally be combined with the subject matter of Example 4, to optionally include the ultrasonic transducer being rotatable about the axis.

Example 6 can include, or can optionally be combined with the subject matter of Examples 1 through 5, to optionally include a second elongate member disposed within the first lumen, and wherein the ultrasonic transducer is disposed within the second elongate member.

Example 7 can include, or can optionally be combined with the subject matter of Examples 1 through 6, to optionally include the first elongate member defining an outer wall region between an outer surface of the first elongate member and the lumen, with the outer wall region having a specified thickness established to permit penetration by acoustic energy from the ultrasound transducer to insonify a region surrounding the outer wall region.

Example 8 can include, or can optionally be combined with the subject matter of Example 7, to optionally include a thickness of the outer wall region being no greater than about 0.5 mm.

Example 9 can include, or can optionally be combined with the subject matter of Example 8, to optionally include a channel located at a proximal end of the first elongate member and defined by the outer wall region and the lumen, and, wherein the channel fluidically couples a proximal end of the first elongate member to the expandable element to permit inflation or deflation of the expandable element using a fluid carried by the channel.

Example 10 can include or use subject matter (such as an apparatus, a method, a means for performing acts, or a device readable medium including instructions that, when performed by the device, can cause the device to perform acts), such as can include or use an apparatus for delivering high dose rate brachytherapy to a tissue region, the apparatus comprising a first elongate member defining a first lumen having an opening at a proximal end of the elongate member and a radiation delivery source device disposed within the first lumen, an expandable element located at a distal end of the first elongate member, a second elongate member that includes an ultrasonic transducer disposed at a distal end of the second elongate member, and a stepper device coupled to the second elongate member, the stepper device being configured to move the ultrasonic transducer in increments along an axis defined longitudinally along the first lumen and is located within the first elongate member, and the ultrasonic transducer generates acoustic energy and receives a signal indicative of scattering or reflection of the acoustic energy.

Example 11 can include, or can optionally be combined with the subject matter of Example 10, to optionally include the signal being used to generate an image of a cavity defined by the tissue region.

Example 12 can include, or can optionally be combined with the subject matter of Examples 10 or 11, to optionally include the radiation source delivery device includes a wire, the high dose rate brachytherapy is delivered via a radiation source coupled to the wire, the radiation source includes a $^{192}$Ir radiation source or a $^{60}$Co radiation source, and the radiation source delivers from 9 grays to 14 grays of radiation over a specified period of time to 1 cm from a surface of the tissue region.

Example 13 can include, or can optionally be combined with the subject matter of Examples 10 through 12, to optionally include the first elongate member defines an interior region at the distal end of the first elongate member, the interior region being located between an interior surface of the first elongate member and the first lumen, and the interior region and the first lumen are at least partially filled with an aqueous solution.

Example 14 can include, or can optionally be combined with the subject matter of Examples 10 to 13, to optionally include the second elongate member being disposed within the first lumen.

Example 15 can include, or can optionally be combined with the subject matter of Examples 10 to 14, to optionally include the first elongate member includes a second lumen, and the radiation source delivery device is disposed within the second lumen.

Example 16 can include, or can optionally be combined with the subject matter of one or any combination of Examples 1 through 15 to include, subject matter (such as an apparatus, a method, a means for performing acts, or a machine readable medium including instructions that, when performed by the machine, that can cause the machine to perform acts), such as can include inflating an expandable element located at a distal end of a brachytherapy applicator using a fluid coupled through a channel defined by the brachytherapy applicator, generating acoustic energy using an ultrasonic transducer located within a first lumen defined by the brachytherapy applicator, receiving a signal indicative of scattering or reflection of the acoustic energy, and generating an image using the received signal, the image indicative of a location of the expandable element within a tissue region.

Example 17 can include, or can optionally be combined with the subject matter of Example 16, to optionally include inserting a radiation source into the brachytherapy applicator to deliver a specified dose of radiation to the tissue region.

Example 18 can include, or can optionally be combined with the subject matter of Examples 16 or 17, to optionally include generating, while the specified dose of radiation is being delivered to the tissue region, additional acoustic energy via the ultrasonic transducer, receiving an additional signal indicative of scattering or reflection of the additional acoustic energy; and generating an additional image based on the additional signal, the additional image indicating a location of the brachytherapy applicator within a cavity defined by an inner surface of the tissue region.

Example 19 can include, or can optionally be combined with the subject matter of Examples 16 through 18, to optionally include the image includes a 3-dimensional (3D) image and the 3D image includes one or more graphical representations indicating at least one of an air pocket located in a cavity defined by an inner surface of the tissue region, a bone proximate to the cavity, or a surface of skin proximate to the cavity.

Example 20 can include, or can optionally be combined with the subject matter of Examples 16 through 19, to optionally include preprocessing data corresponding to a plurality of signals received from the ultrasonic transducer before generating the image by at least one of: applying at least one speckle reduction technique, performing histogram optimization to adjust brightness and contrast of features included in the image, or enhancing edge features included in the image.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, comprising:
a first elongate member defining a first lumen having an opening at a proximal end of the first elongate member;
an expandable element located at a distal end of the first elongate member;
a second elongate member disposed within the first lumen; and
an ultrasonic transducer disposed within the second elongate member and positionable along the second elongate member.

2. The apparatus of claim 1, comprising a radiation source delivery device located within the first lumen and positionable along the first elongate member.

3. The apparatus of claim 1, wherein the first elongate member includes a second lumen and a radiation source delivery device is located within the second lumen.

4. The apparatus of claim 1, comprising a stepper device coupled to the ultrasonic transducer, the stepper device being configured to move the ultrasonic transducer in specified increments along an axis defined longitudinally along the first lumen and is located within the first elongate member.

5. The apparatus of claim 4, wherein the ultrasonic transducer is rotatable about the axis.

6. The apparatus of claim 4, wherein the stepper device is located external to the first elongate member.

7. The apparatus of claim 1, wherein:
the first elongate member defines an outer wall region between an outer surface of the first elongate member and the first lumen, the outer wall region having a specified thickness established to permit penetration by acoustic energy from the ultrasonic transducer to insonify a region surrounding the outer wall region.

8. The apparatus of claim 7, wherein a thickness of the outer wall region is no greater than about 0.5 mm.

9. The apparatus of claim 8, comprising a channel located at a proximal end of the first elongate member and defined by the outer wall region and the first lumen, and, wherein the channel fluidically couples a proximal end of the first elongate member to the expandable element to permit inflation or deflation of the expandable element using a fluid carried by the channel.

10. An apparatus for delivering high dose rate brachytherapy to a tissue region, the apparatus comprising:
a first elongate member defining a first lumen having an opening at a proximal end of the first elongate member and a radiation source delivery device disposed within the first lumen;
an expandable element located at a distal end of the first elongate member;
a second elongate member disposed within the first lumen, wherein the second elongate member includes an ultrasonic transducer disposed at a distal end of the second elongate member and the ultrasonic transducer is positionable along the second elongate member; and
a stepper device coupled to the second elongate member, the stepper device being configured to move the ultrasonic transducer in increments along an axis defined longitudinally along the first lumen and is located within the first elongate member; and
wherein the ultrasonic transducer generates acoustic energy and receives a signal indicative of scattering or reflection of the acoustic energy.

11. The apparatus of claim 10, wherein the signal is used to generate an image of a cavity defined by the tissue region.

12. The apparatus of claim 10, wherein:
the radiation source delivery device includes a wire;
the high dose rate brachytherapy is delivered via a radiation source coupled to the wire;
the radiation source includes a $^{192}$Ir radiation source or a $^{60}$Co radiation source; and
the radiation source delivers from 9 grays to 14 grays of radiation over a specified period of time to 1 cm from a surface of the tissue region.

13. The apparatus of claim 10, wherein:
the first elongate member defines an interior region at the distal end of the first elongate member, the interior region being located between an interior surface of the first elongate member and the first lumen; and
the interior region and the first lumen are at least partially filled with an aqueous solution.

14. The apparatus of claim 10, wherein the stepper device is located external to the first elongate member.

15. The apparatus of claim 10, wherein:
the first elongate member includes a second lumen; and
the radiation source delivery device is disposed within the second lumen.

16. A method comprising:
inflating an expandable element located at a distal end of a brachytherapy applicator using a fluid coupled through a channel defined by the brachytherapy applicator, the brachytherapy applicator including:
a first elongate member defining a first lumen having an opening at a proximal end of the first elongate member;
a second elongate member disposed within the first lumen; and
an ultrasonic transducer disposed within the second elongate member and positionable along the second elongate member;
generating acoustic energy using an ultrasonic transducer located within a first lumen defined by the brachytherapy applicator;
receiving a signal indicative of scattering or reflection of the acoustic energy; and
generating an image using the received signal, the image indicative of a location of the expandable element within a tissue region.

17. The method of claim 16, comprising:
inserting a radiation source into the brachytherapy applicator to deliver a specified dose of radiation to the tissue region.

18. The method of claim 17, further comprising:
generating, while the specified dose of radiation is being delivered to the tissue region, additional acoustic energy via the ultrasonic transducer;
receiving an additional signal indicative of scattering or reflection of the additional acoustic energy; and
generating an additional image based on the additional signal, the additional image indicating a location of the brachytherapy applicator within a cavity defined by an inner surface of the tissue region.

19. The method of claim 16, wherein the image includes a 3-dimensional (3D) image and the 3D image includes one or more graphical representations indicating at least one of an air pocket located in a cavity defined by an inner surface of the tissue region, a bone proximate to the cavity, or a surface of skin proximate to the cavity.

20. The method of claim 16, further comprising preprocessing data corresponding to a plurality of signals received from the ultrasonic transducer before generating the image by at least one of:
- applying at least one speckle reduction technique;
- performing histogram optimization to adjust brightness and contrast of features included in the image; or
- enhancing edge features included in the image.

* * * * *